(12) United States Patent
Napolitano et al.

(10) Patent No.: US 8,900,100 B2
(45) Date of Patent: Dec. 2, 2014

(54) SYSTEM AND METHOD FOR PROMOTING AND TRACKING PHYSICAL ACTIVITY AMONG A PARTICIPATING GROUP OF INDIVIDUALS

(75) Inventors: Frank Napolitano, Philadelphia, PA (US); Andrew Greenberg, Philadelphia, PA (US); Christian Ludwig, Philadelphia, PA (US)

(73) Assignee: Global Affiliates, Inc., Philadelphia, PA (US)

( * ) Notice: Subject to any disclaimer, the term of this patent is extended or adjusted under 35 U.S.C. 154(b) by 555 days.

(21) Appl. No.: 13/396,205

(22) Filed: Feb. 14, 2012

(65) Prior Publication Data

US 2013/0102439 A1    Apr. 25, 2013

Related U.S. Application Data

(63) Continuation-in-part of application No. 13/280,954, filed on Oct. 25, 2011, now Pat. No. 8,517,897.

(51) Int. Cl.
*A63B 71/00*    (2006.01)
*A61B 5/103*    (2006.01)
*A61B 5/117*    (2006.01)

(52) U.S. Cl.
USPC ............................................. 482/8; 600/595

(58) Field of Classification Search
CPC ........... A63B 24/0059; A63B 24/0062; A63B 24/084; A63B 71/0616; A63B 2024/0062; A63B 2024/0068; A63B 2024/0075

USPC .............. 705/2, 14.1; 434/247, 255; 600/300, 600/587, 595; 700/91–93; 482/1–9, 482/901–902
IPC ............. A63B 15/02,71/00; A61B 5/103, 5/117
See application file for complete search history.

(56) References Cited

U.S. PATENT DOCUMENTS

| | | | |
|---|---|---|---|
| 8,012,064 B2* | 9/2011 | Martens ............................ | 482/8 |
| 8,070,655 B1* | 12/2011 | Napolitano et al. .............. | 482/8 |
| 8,172,722 B2* | 5/2012 | Molyneux et al. ................ | 482/1 |
| 8,231,506 B2* | 7/2012 | Molyneux et al. ................ | 482/1 |
| 8,517,897 B2* | 8/2013 | Napolitano et al. .............. | 482/8 |
| 8,533,620 B2* | 9/2013 | Hoffman et al. ............... | 715/772 |
| 2010/0184564 A1* | 7/2010 | Molyneux et al. ................ | 482/1 |
| 2011/0029241 A1* | 2/2011 | Miller et al. ................... | 701/220 |

* cited by examiner

*Primary Examiner* — Oren Ginsberg
(74) *Attorney, Agent, or Firm* — Barnes & Thornburg LLP; Thomas J. McWilliams; Edward F. Behm, Jr.

(57) ABSTRACT

A system and method of tracking physical activity of a person in order to help motivate that person to add more exercise to their lives. Each participant is provided a motion sensor that detects forces incurred by the participant. The motion sensor creates electronic data that corresponds to the forces detected. The data is analyzed to determine whether or not exercise has been performed. The analysis can also determine the type of exercise performed, when the exercise was performed, and the duration of the exercise performed.

15 Claims, 51 Drawing Sheets

| Participant: | John Baker |
| --- | --- |
| Location: | Boston, MA |
| Age: | 43 |
| Gender: | Male |
| Restrictions: | None |
| ID: | 85965651 |

Fig. 3A

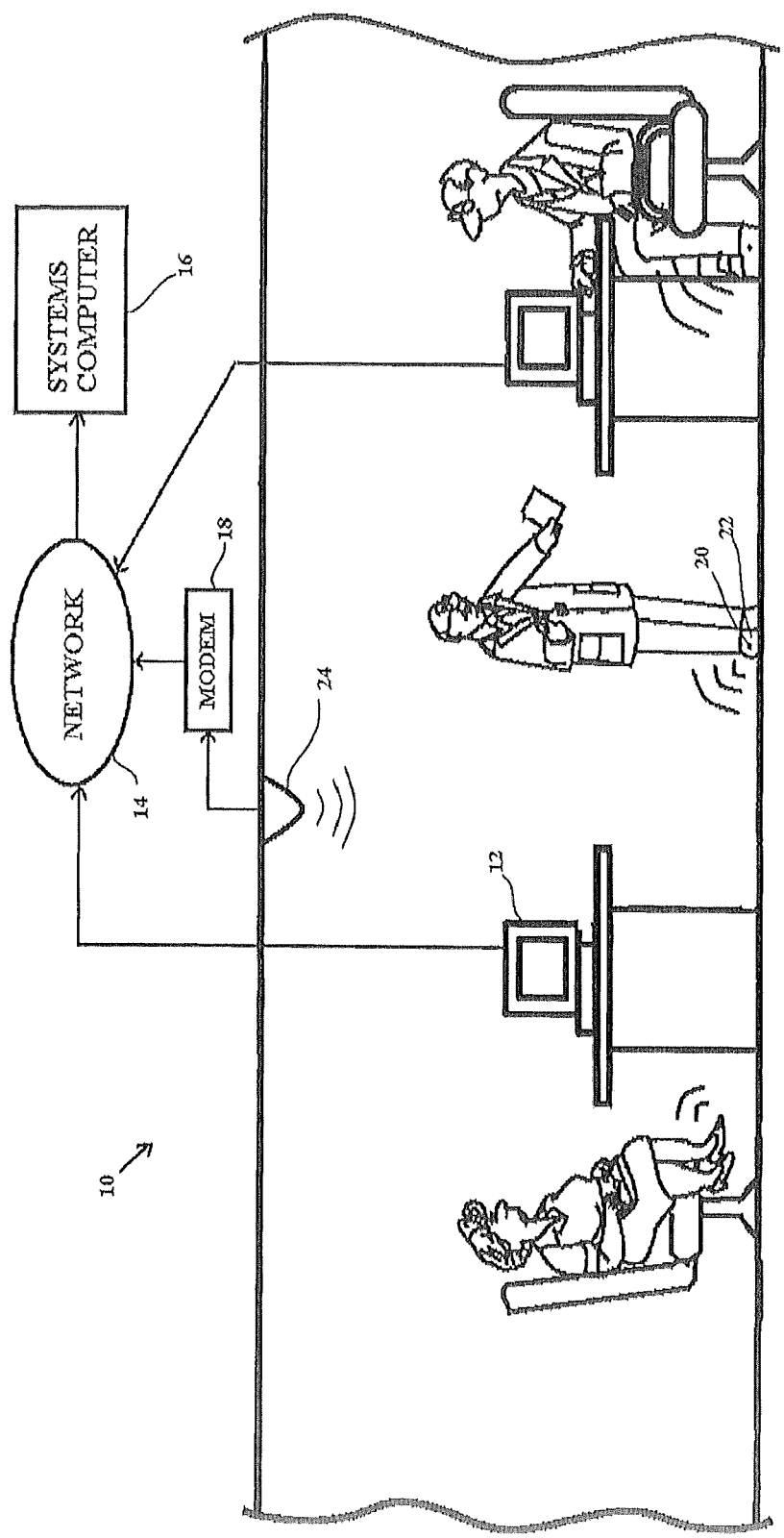

[Logout] Welcome, Kandice

Home | My Account | Resources | Challenges | Help
View My Challenges and Teams | Join a Challenge or Team | Create a New Challenge or Team Last Updated: 3 days ago
Current Time:

My Challenges

Q1 Regional Challenge -- Challenge still running
Team Average Accumulation Competition  *Hide*

March Madness Challenge -- Challenge still running
Individual Accumulation Competition  *Hide*

NAME: March Madness Challenge

DEFINITION: Most steps accumulated between 3/1/11 and 3/31/11. All steps must be off loaded by 4/4/11.

DESCRIPTION: Hey guys -- the winner of this challenge gets four box seat tickets to the Spurs vs. Lakers game on April 12.  *Edit*
OWNER: kturner@globalfit.com ⓘ Info                                    *See All/Export to Excel*

Current Participants

| User Name | Steps | |
|---|---|---|
| 1 CAMcDonald | 43,018 | ⊗ |
| 2 dennisrupp@hotmail.com | 42,526 | ⊗ |
| 3 Davidesp | 41,016 | ⊗ |
| 4 Ahashmi | 38,954 | ⊗ |
| 5 bcallan@globalfit.com | 37,733 | ⊗ |
| ... | | |
| 16 Kturner1 | 33,639 | ⊗ |
| 17 dbutler@globalfit.com | 33,387 | ⊗ |
| 18 lmallory@globalfit.com | 32,962 | ⊗ |
| 17 Fdanay | 31,198 | ⊗ |

*Invite Additional Participants*

60 Mile Training - Challenge still running
Individual Accumulation Achievement  *Hide*

Cory vs The World - Challenge still running
Team Total Accumulation Competition  *Hide*

February Challenge - Winner: dbutler@globalfit.com
Individual Race Competition  *Hide*

My Teams

Green Team
Owner/Captain: kturner@globalfit.com  *Hide*

Harry and the Potters
Owner/Captain: agreenberg@globalfit.com  *Hide*

*Show Hidden Challenges/Teams* ⓐ

Last Updated: 3 days ago

[Logout] Welcome, Kandice

Home | My Account | Resources | Challenges | Help
View My Challenges and Teams | Join a Challenge or Team | Create a New Challenge or Team Current Trip: Quebec City, Canada

My Challenges

Q1 Regional Challenge -- Challenge still running
Team Average Accumulation Competition                     *Hide*

March Madness Challenge -- Challenge still running
Individual Accumulation Competition                        *Hide*

60 Mile Training - Challenge still running
Individual Accumulation Achievement                        *Hide*

Cory vs The World - Challenge still running
Team Total Accumulation Competition                        *Hide*

February Challenge -- Winner: dbutler@globalfit.com
Individual Race Competition                                *Hide*

My Teams

Green Team
Owner/Captain: kturner@globalfit.com                       *Hide*

Harry and the Potters
Owner/Captain: agreenberg@globalfit.com                    *Hide*

*Show Hidden Challenges/Teams*

---

NAME: March Madness Challenge

DEFINITION: Most steps accumulated between 3/1/11 and 3/31/11. All steps must be off loaded by 4/4/11.

DESCRIPTION: Hey guys -- the winner of this challenge gets four box seat tickets to the Spurs vs. Lakers game on April 12.

OWNER: kturner@globalfit.com

ⓘ Info                                *See All/Export to PDF*

Current Participants

| User Name | Steps |
|---|---|
| CAMcDonald | 43,018 |
| dennisrings@hotmail.com | 42,526 |
| Davidesp | 41,016 |
| Ahashmi | 38,954 |
| bcallan@globalfit.com | 37,723 |
| kstumit | 33,639 |
| dbutler@globalfit.com | 33,387 |
| lmallory@globalfit.com | 32,962 |
| Febenay | 31,198 |

Last Updated: 3 days ago  
[Logout] Welcome, Kandice

Home | My Account | Resources | Challenges | Help  
View My Challenges and Teams | Join a Challenge or Team | Create a New Challenge or Team Current Trip: Cambodia, Experience

Create a New Challenge or Team

Click here to read the challenge and teams planning guide. When you are ready, answer each question to create your challenge or team.

Write a message or a description for the challenge participants.

SUMMARY

This is a challenge that is by invitation only. It is a competitive challenge that is an accumulation of steps by individuals between 3/1/11 and 12/31/11. All steps must be offloaded by 4/4/11 in order to count towards this challenge.

The name of the challenge is: March Madness Challenge.

Challenge Description:

[ Submit ]

*Back*  *Start Over*

Fig. 30

Last Updated: 3 days ago [Logout] Welcome, Kandice

Home | My Account | Resources | Challenges | Help
View My Challenges and Teams | Join a Challenge or Team | Create a New Challenge or Team Current Trip: Create Your Avatar

Create a New Challenge or Team

Click here to read the challenge and teams planning guide. When you are ready, answer each question to create your challenge or team.

Invite New Participants
Select: All, None
Filter by Letter: ALL ▼

☐ Achey, Amy ( aachey@globalfit.com )
☐ Barnes, Jessica ( jbarnes@globalfit.com )
☐ Blum, Karyn ( Karynnew )
☐ Braverman, Stefany ( stbrav )
☐ Brown, Angela ( abrown0266 )
☐ Buckley, Christine ( cbuckley@globalfit.com )
☐ Clements, Julian ( wallstreetkid06@yahoo.com )
☐ Esposito, Nina ( davidesp )
☐ Fitzpatrick, Joe ( jfitzpatrick@globalfit.com )
☐ Foxx, Julie ( JulieFoxx2004 )
☐ Gipprich, Matthew ( mattgipp )
☐ Greenberg, Andy ( agreenberg )
☐ Harris, Aqueelah ( acamacho@globalfit.com )
☐ Hashmi, Abrar ( ahashmi )
☐ Hunt, Kim ( khunt@globalfit.com )
☐ Kilcrest, Sharon ( kilcrest@comcast.net )

Add Selected Participants

NAME: March Madness Challenge

DEFINITION: Most steps accumulated between 3/1/11 and 3/31/11. All steps must be off loaded by 4/4/11.

DESCRIPTION: Hey guys – the winner of this challenge gets four box seat tickets to the Spurs vs. Lakers game on April 12.   *Edit*

OWNER: kturner@globalfit.com

Current Participants:
Name – User Name
McDonald, Corey ( CAMcDonald )
Callan, Beth ( bcallan@globalfit.com )
Butler, David ( dbutler@globalfit.com )
Daney, Frank ( fdany )

Submit & Automatically Enroll Participants

Submit & Require Participants To Accept Invitation

Fig. 31

[Logout] Welcome, Kandice
Last Updated: 3 days ago

Home | My Account | Resources | Challenges | Help
View My Challenges and Teams | Join a Challenge or Team | Create a New Challenge or Team

Create a New Challenge or Team

Click here to read the challenge and teams planning guide. When you are ready, answer each question to create your challenge or team.

Invite New Participants

Search by last name, user name, or email address and then click on the name to add the participant. Please note: If you wish to be in this challenge/team, you must add yourself as well.

[ Turner ]   [ Search ]

Turner, Kandice
Turner, Kenny

NAME: March Madness Challenge

DEFINITION: Most steps accumulated between 3/1/11 and 3/31/11. All steps must be off loaded by 4/4/11.

DESCRIPTION: Hey guys – the winner of this challenge gets four box seat tickets to the Spurs vs. Lakers game on April 12.   *Edit*

OWNER: kturner@globalfit.com

Current Participants

| Name - User Name |
|---|
| McDonald, Cory (CMcDonald) |
| Callan, Beth (bcallan@globalfit.com) |
| Butler, David (dbutler@globalfit.com) |
| Danay, Frank (fdanay) |

[ Submit ]

SYSTEM AND METHOD FOR PROMOTING AND TRACKING PHYSICAL ACTIVITY AMONG A PARTICIPATING GROUP OF INDIVIDUALS

CROSS-REFERENCE TO RELATED APPLICATION

This application claims the benefit of priority as a continuation-in-part of U.S. patent application Ser. No. 13/280,954, filed on Oct. 25, 2011, the entirety of each of which applications is incorporated herein by reference as if set forth in its respective entirety.

BACKGROUND OF THE INVENTION

1. Field of the Invention

In general, the present invention relates to systems and methods that are used to track the health and wellbeing of people within a targeted group. More particularly, the present invention relates to systems and methods that utilize interactive software to both promote and track physical activity among participants in the targeted group.

2. Description of the Background

It is a well-established fact that people generally live longer, healthier lives if they get regular physical activity. It is also a well-established fact that people are more likely to start and continue a lifestyle of physical activity if they have peers and friends that are also participating in that exercise program. Recognizing the above stated facts, many companies have developed employee exercise programs. The hope is that these programs would lead to healthier employees and healthier employees would use less sick days and have lower healthcare costs. By offering exercise programs at work, it is hoped that employees would exercise with peers and would benefit from the support of peers.

Difficulties develop, however, when the management of a company tries to develop exercise programs for their employees. The problem is that many people are not yet behaviorally ready to "exercise" and that not all of those who are enjoy the same types of exercise. As such, a company gym may only appeal to some employees, while a company softball team may appeal to others. Recognizing that different people like different things, exercise programs have been developed that are highly flexible to fit the varied needs and wants of a company's employees. In such exercise programs, the management of a company does not concern itself with what physical activity is being performed. Rather, the company just monitors whether physical activity is being performed and often offers incentives to employees to start and maintain physical activity as part of their daily routines.

The most common way that companies monitor whether or not an employee is performing exercise is to provide the employees with interactive computer software. Using the software, an employee can enter what exercise has been performed. This information is then stored in a database for access by the company. Such exercise monitoring software systems are exemplified by U.S. Patent Application Publication No. 2006/0287883 to Turgis, entitled Interactive Internet Supported Health And Fitness Management System; U.S. Patent Application Publication No. 2007/0072154 to Kaufman, entitled Lifesytle Coach Behavior Modification System; and U.S. Patent Application Publication No. 2007/0100595 to Earles, entitled Behavior Monitoring And Reinforcement System and Method.

The problem associated with such prior art exercise monitoring software systems is that the systems require that an individual manually input data into a computer to inform the computer of what exercise has been performed. Since many of these systems provide rewards for exercise, there is a good incentive for people to lie about exercising or exaggerate in order to receive the reward. Furthermore, people quickly grow tired of tasks in which they are not interested. Employees that must voluntarily enter and log their daily exercise routines may quickly develop user fatigue. Employees may forget to enter data daily and when they do enter data, that data may contain guesses and inaccurate remembrances of days past.

Alternatively, some companies use activity tracking technology that "docks" to a computer to offload the activity data. The problem associated with this type of connection is that it often is inconvenient or cumbersome for the individual to gain access to the computer and as such the participation levels drop off quickly.

Another problem associated with such prior art exercise systems is that it is difficult for an employee to equate different exercises with one another. For example, how may miles of kayaking equate to how many hours of playing tennis? This difficultly in equating exercises makes it very difficult to establish goals for rewards. It also makes it very difficult to set up challenges and competitions among participants that would promote further exercise.

The notion of challenges and competitions is well established, wherein individuals can compete with each other or create teams that compete against one another. However, when working with an organization that has thousands of employees and hundreds of different groups, it has historically been very difficult for an administrator to easily turn those groups into competitive fitness teams, and/or to create challenges between and among such groups and/or teams. This has significantly limited the ability of organizations to leverage the natural social support network of departments, internal work groups, project colleagues, and/or geographic locations into a healthier organizational culture.

A need therefore exists for an exercise system that both passively and accurately monitors the amount of exercise performed by an individual, thereby reducing cheating and user fatigue. A need also exists for an exercise system where all exercises are automatically reduced to comparable units, thereby enabling all exercises to be compared for use in challenges and competitions. A need also exists for an exercise system whereby data collected automatically and passively offloads to a central database, thereby eliminating the need for active intervention by the individual to participate in the program. Finally, a need also exists to allow an administrator to easily set up challenges and competitions between varying sizes and numbers of groups. These needs are met by the present invention as described and claimed below.

SUMMARY OF THE INVENTION

The present invention is a system and method of tracking physical activity of a person in order to help motivate that person to add more exercise to their lives. Each participant is provided a motion sensor that detects forces incurred by the participant. The motion sensor creates electronic data that corresponds to the forces detected. The motion detector is worn by the participant at some point on the body both when the participant is exercising and when the participant is not exercising.

The motion sensor has the ability to passively transmit the data it collects. The data is analyzed. During the analysis of the data, it can be determined whether or not physical activity has been performed. The analysis can also determine the type of exercise performed, when the exercise was performed, and the duration of the exercise performed.

The exercise of each participant can be converted into a preselected caloric expenditure unit or equivalent steps for a specific type of exercise. In this manner, the exercise types of all participants can be accurately compared and applied to common exercise goals or exercise competitions. If an exercise goal is achieved, participants are rewarded with reward points in an amount proportionate to difficulties in achieving the exercise goal. The reward points can be used as payment for selected goods and services that promote a healthy lifestyle.

The system may additionally allow an administrator to take a file that has a multitude of groupings for each participant(s), and to turn those common groupings into teams. Those teams can then be entered into exercise competitions in which the winning team members are rewarded for their collective or respective individual achievement. In this way, members of a team may be motivated to encourage each other to be more physically active and to thereby achieve a healthier lifestyle.

Thus, the present invention provides: an exercise system that both passively and accurately monitors the amount of exercise performed by an individual, thereby reducing cheating and user fatigue; an exercise system where all exercises are automatically reduced to comparable units, thereby enabling all exercises to be compared for use in challenges and competitions; an exercise system whereby data collected automatically and passively offloads to a central database, thereby eliminating the need for active intervention by the individual to participate in the program; and a system and method to allow an administrator to easily set up challenges and competitions between varying sizes and numbers of groups.

BRIEF DESCRIPTION OF THE DRAWINGS

For a better understanding of the present invention, reference is made to the following description of an exemplary embodiment thereof, considered in conjunction with the accompanying drawings, in which:

FIG. 3A is a sample eligibility file from a company with pre-defined sets of groups for use with the present invention system;

FIG. 3B is a schematic view of an office containing the present invention system;

FIG. 11 is a screen shot illustrating exemplary aspects of the present invention;

FIG. 12 is a screen shot illustrating exemplary aspects of the present invention;

FIG. 13 is a screen shot illustrating exemplary aspects of the present invention;

FIG. 14 is a screen shot illustrating exemplary aspects of the present invention;

FIG. 15 is a screen shot illustrating exemplary aspects of the present invention;

FIG. 16 is a screen shot illustrating exemplary aspects of the present invention;

FIG. 17 is a screen shot illustrating exemplary aspects of the present invention;

FIG. 18 is a screen shot illustrating exemplary aspects of the present invention; and FIG. 19 is a screen shot illustrating exemplary aspects of the present invention;

Figure 24:
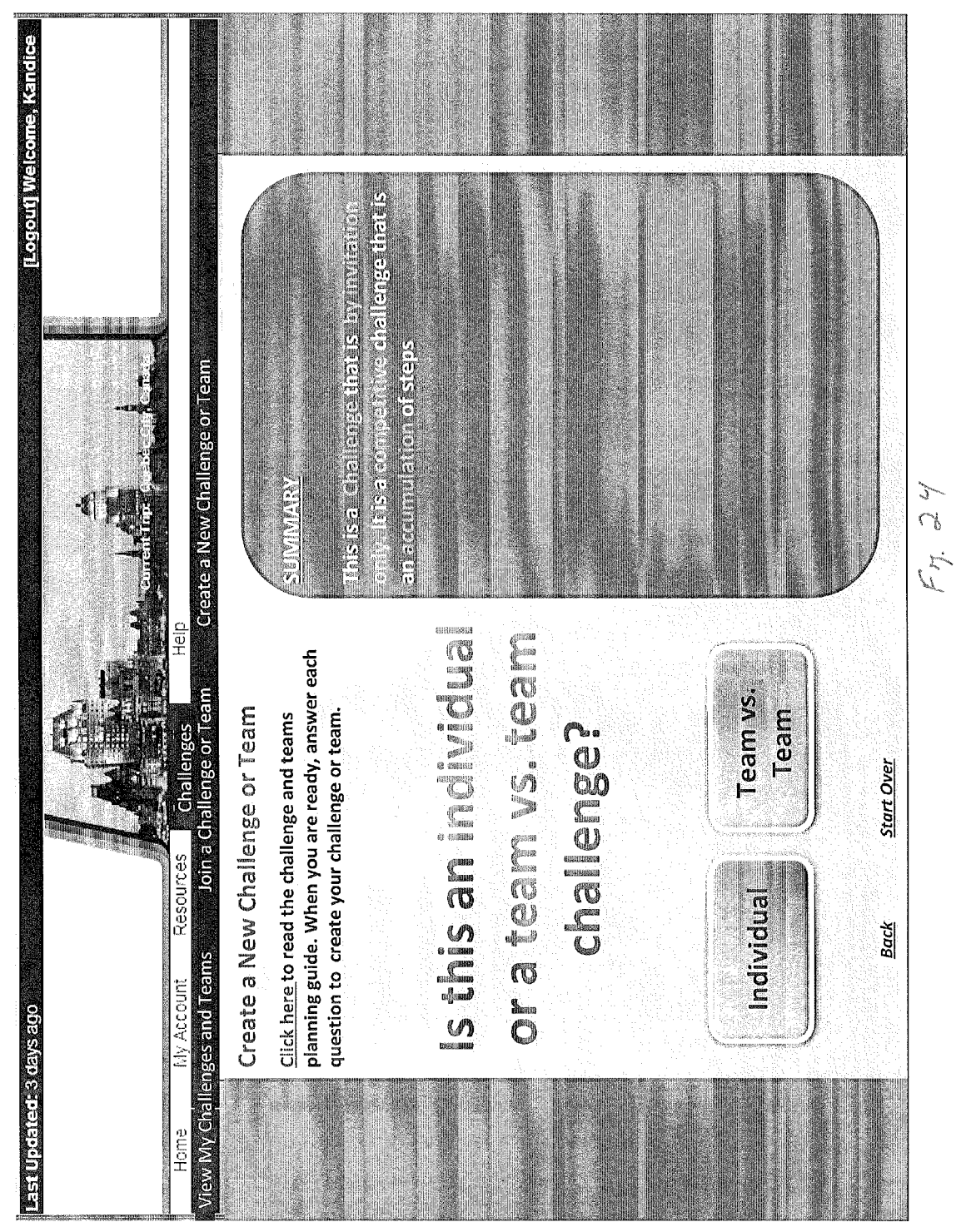

FIG. 24 is a screen shot illustrating exemplary aspects of the present invention;

Figure 25:
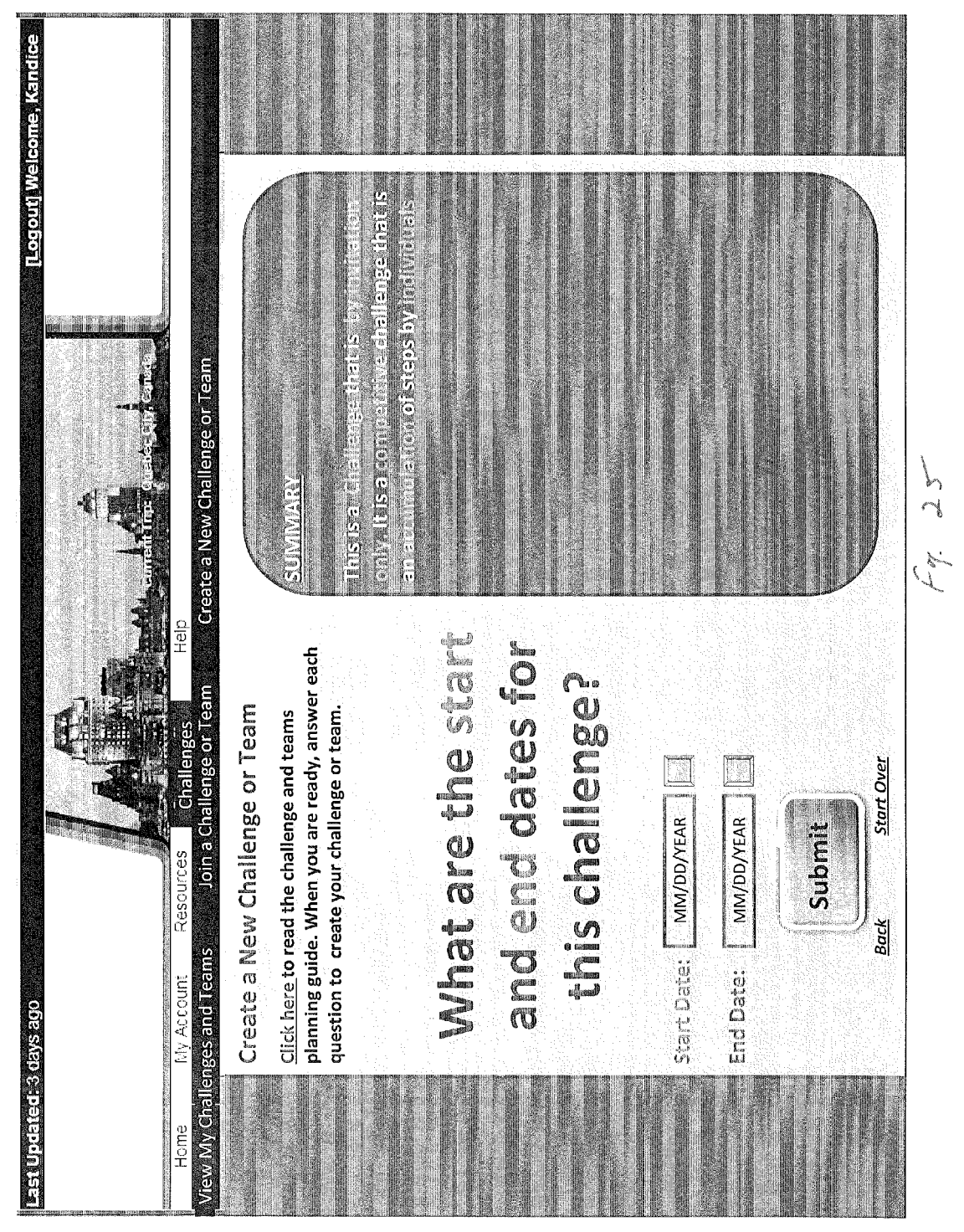

FIG. 25 is a screen shot illustrating exemplary aspects of the present invention;

FIG. 26 is a screen shot illustrating exemplary aspects of the present invention; and FIG. 27 is a screen shot illustrating exemplary aspects of the present invention;

FIG. 28 is a screen shot illustrating exemplary aspects of the present invention;

FIG. 30 is a screen shot illustrating exemplary aspects of the present invention;

FIG. 31 is a screen shot illustrating exemplary aspects of the present invention;

Figure 37:
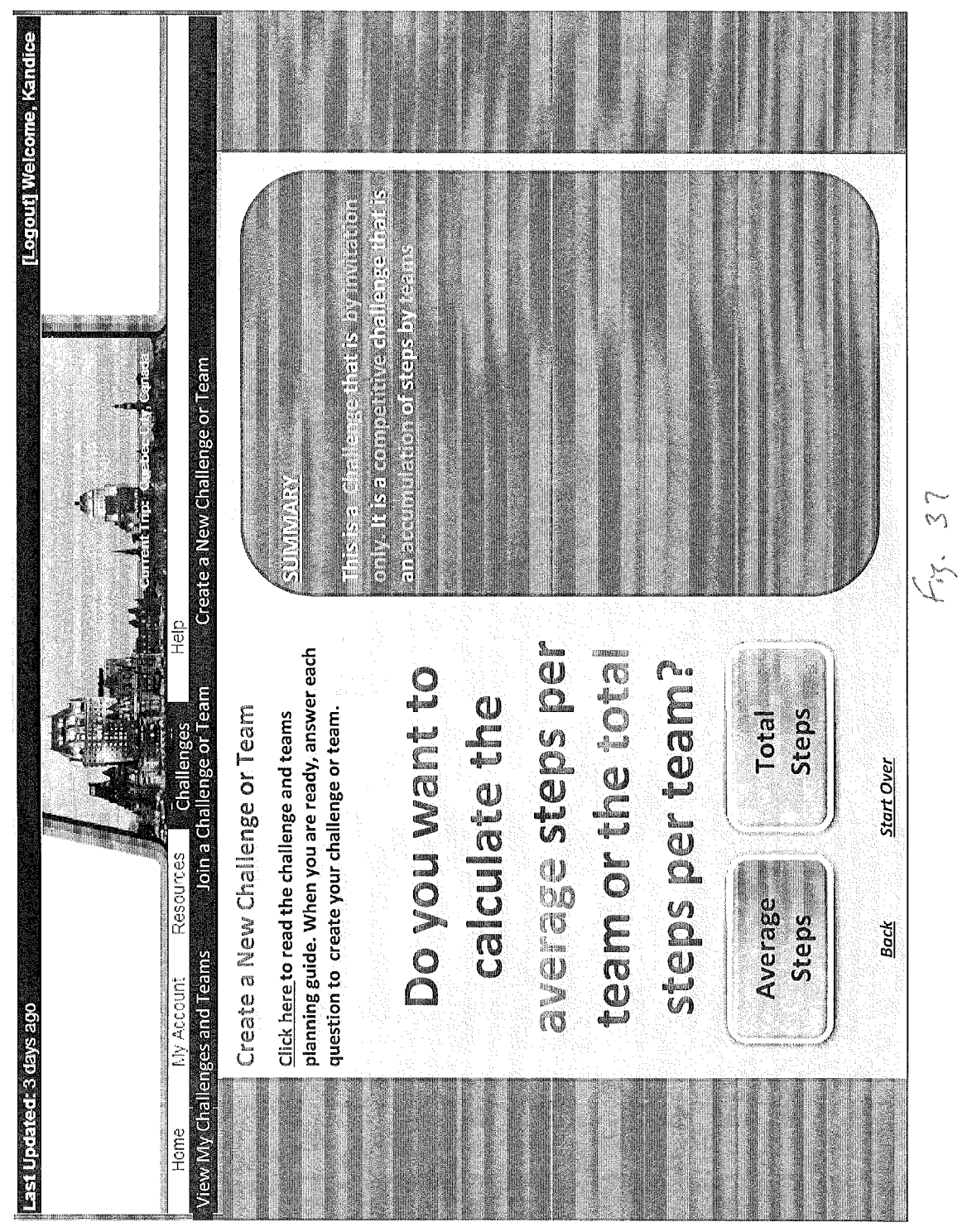

FIG. 37 is a screen shot illustrating exemplary aspects of the present invention;

Figure 38:
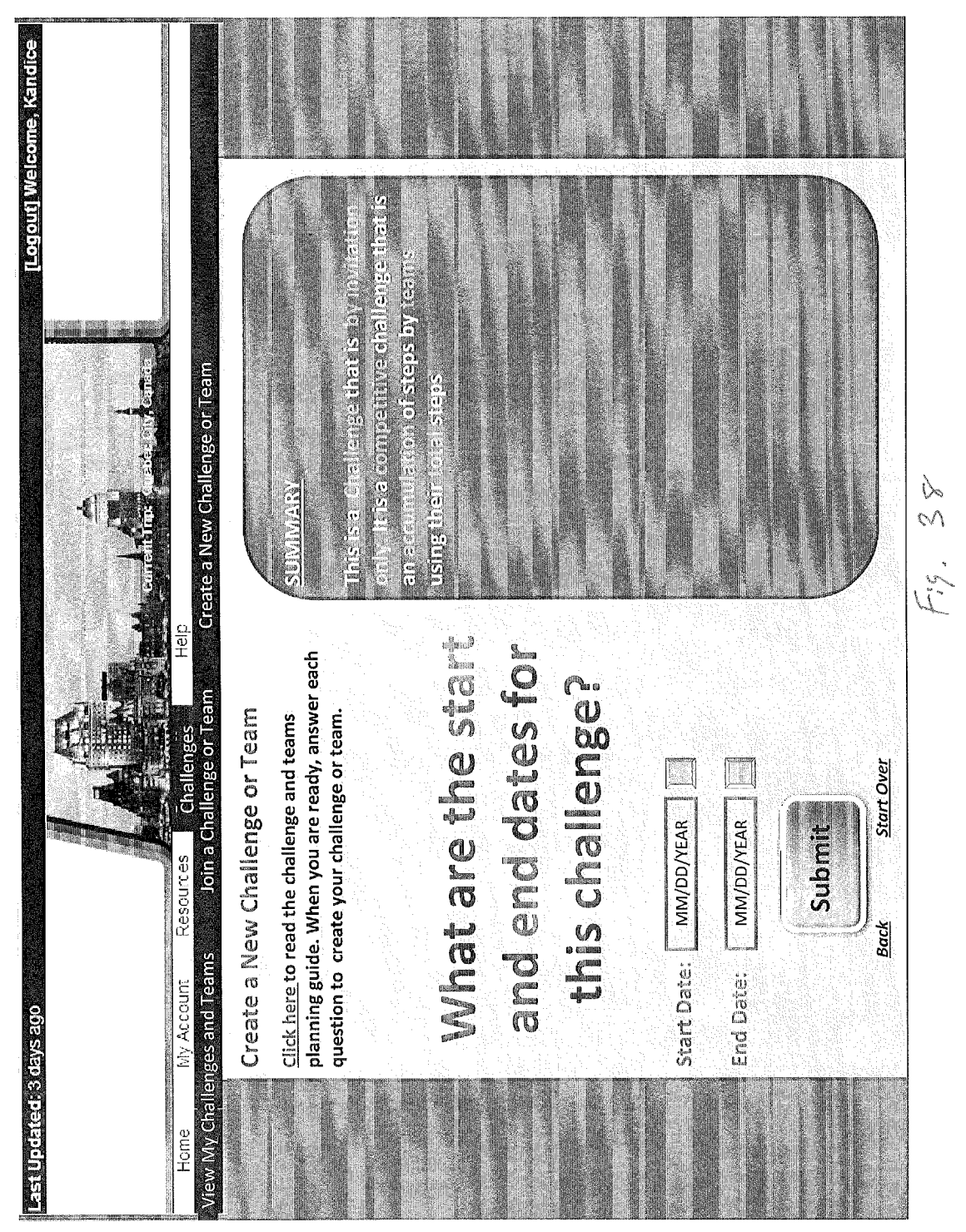

FIG. 38 is a screen shot illustrating exemplary aspects of the present invention;

Figure 39:
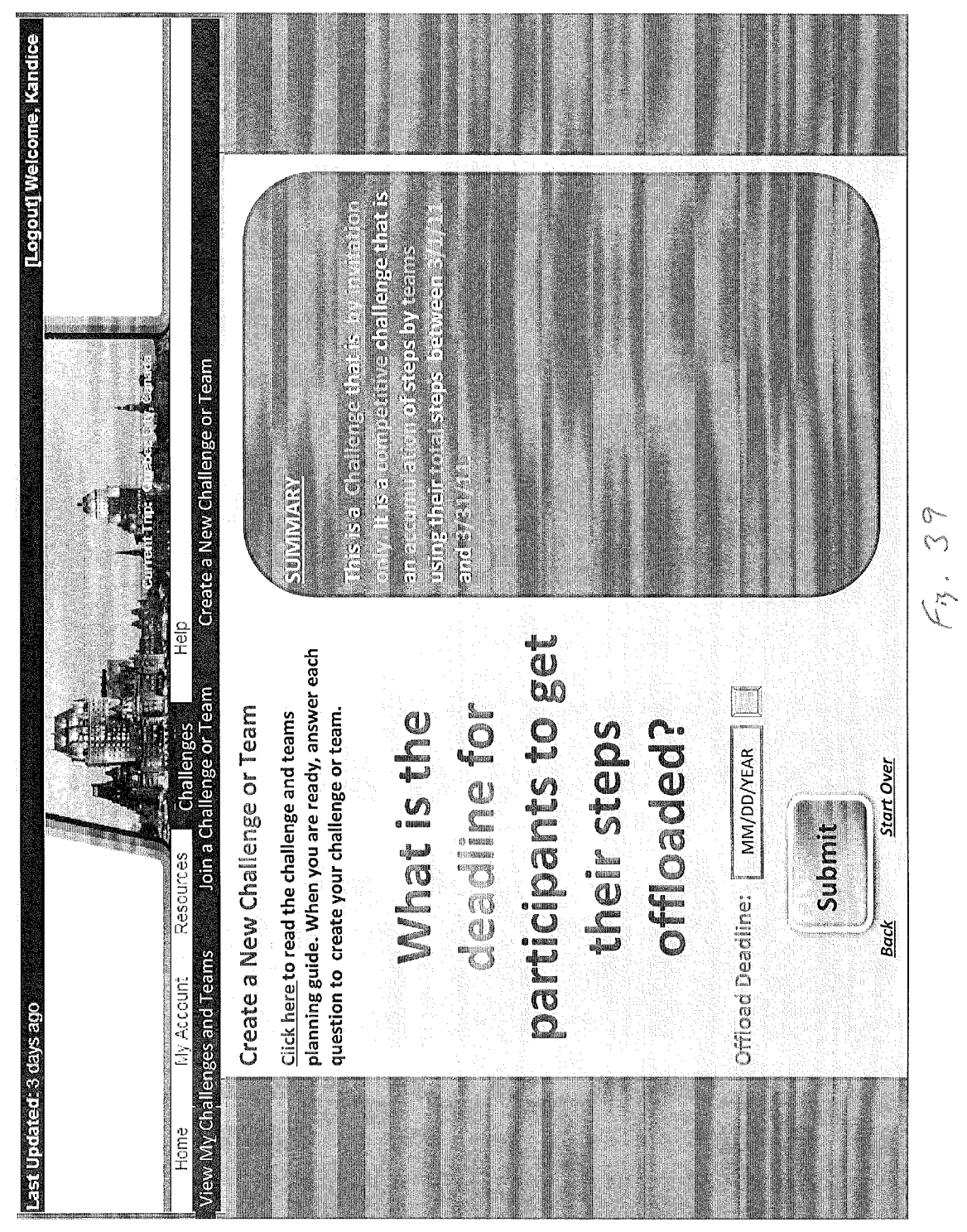

FIG. 39 is a screen shot illustrating exemplary aspects of the present invention;

Figure 41:
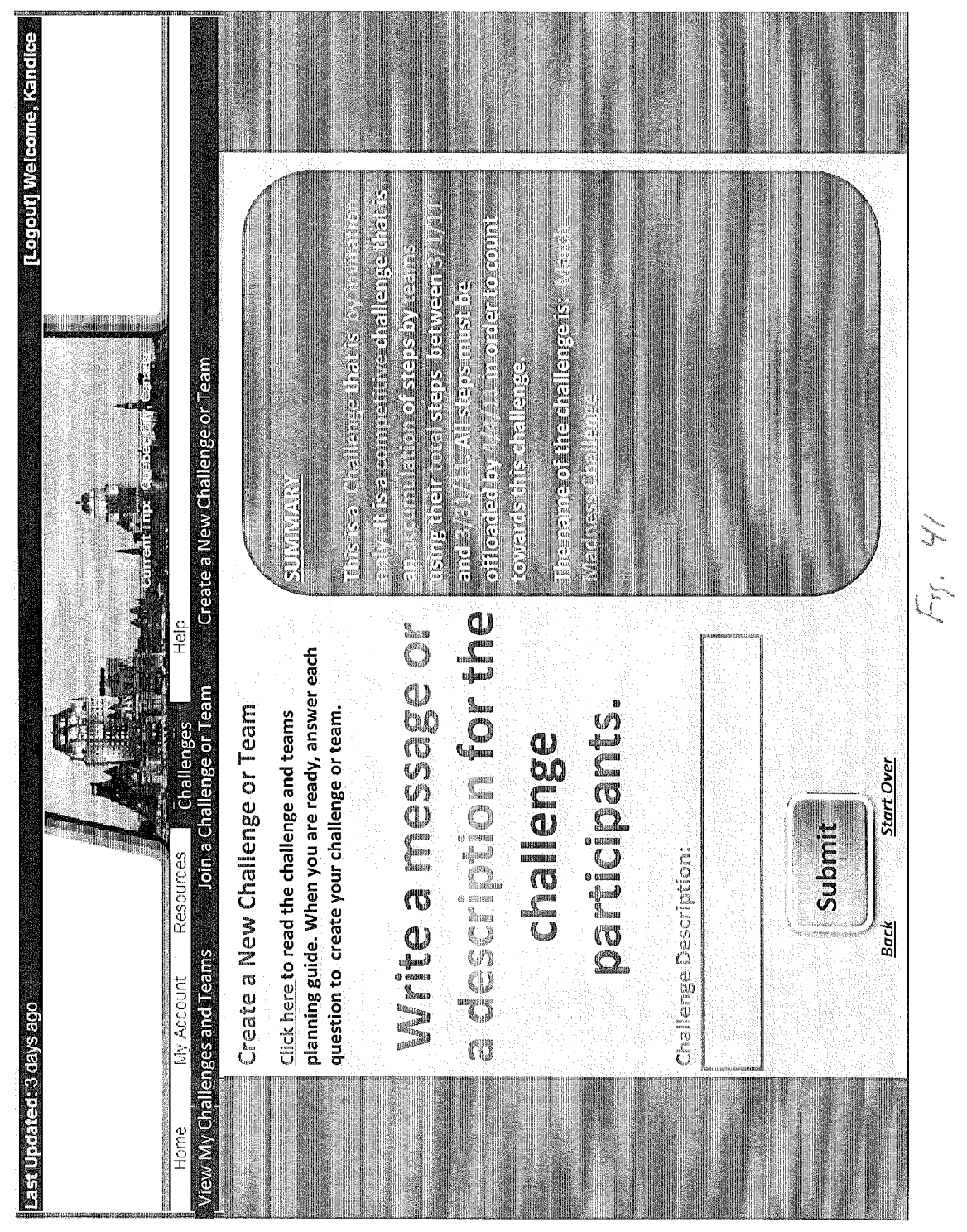

FIG. 41 is a screen shot illustrating exemplary aspects of the present invention;

FIG. 47 is a screen shot illustrating exemplary aspects of the present invention;

Figure 48:
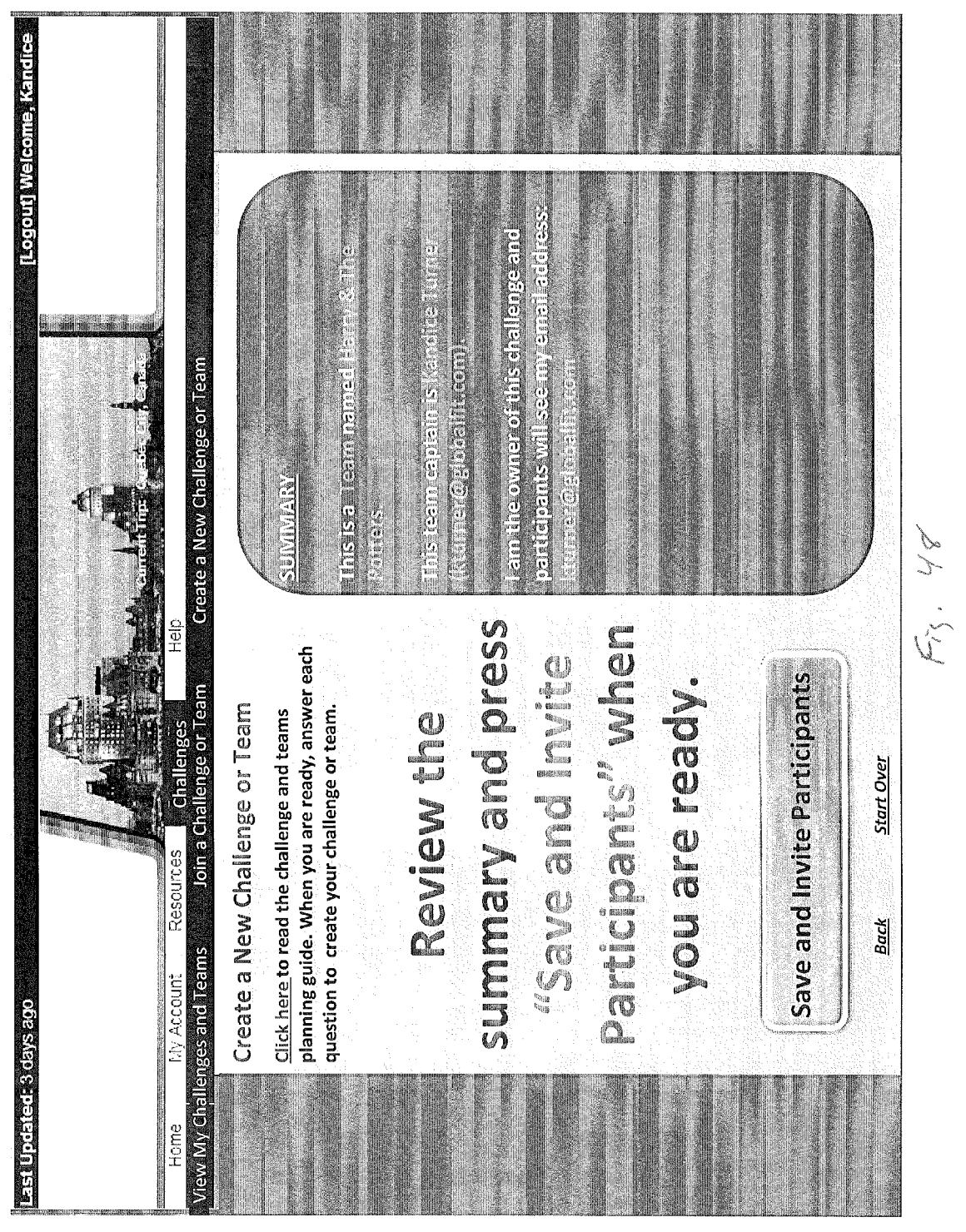

FIG. 48 is a screen shot illustrating exemplary aspects of the present invention;

Figure 49:
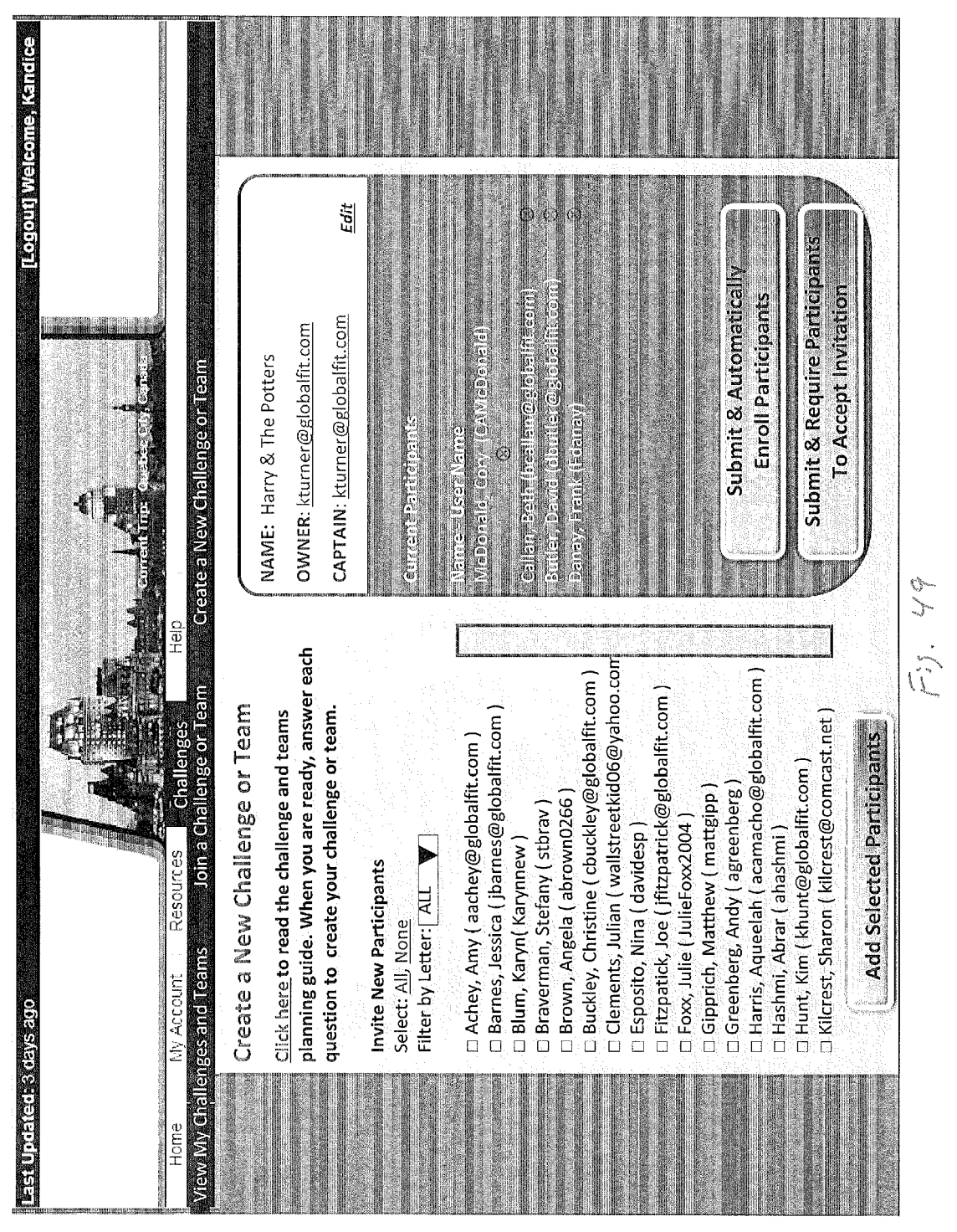

FIG. 49 is a screen shot illustrating exemplary aspects of the present invention.

DETAILED DESCRIPTION OF THE INVENTION

Although the present invention system can be used by many different user groups, such as schools, health clubs, or a community of registered online users, the embodiment illustrated shows the system being used by an employer to promote exercise among its employees. This embodiment is selected in order to set forth the best mode contemplated for the invention. The illustrated embodiment, however, is merely exemplary and should not be considered a limitation when interpreting the scope of the appended claims.

Figure 1:
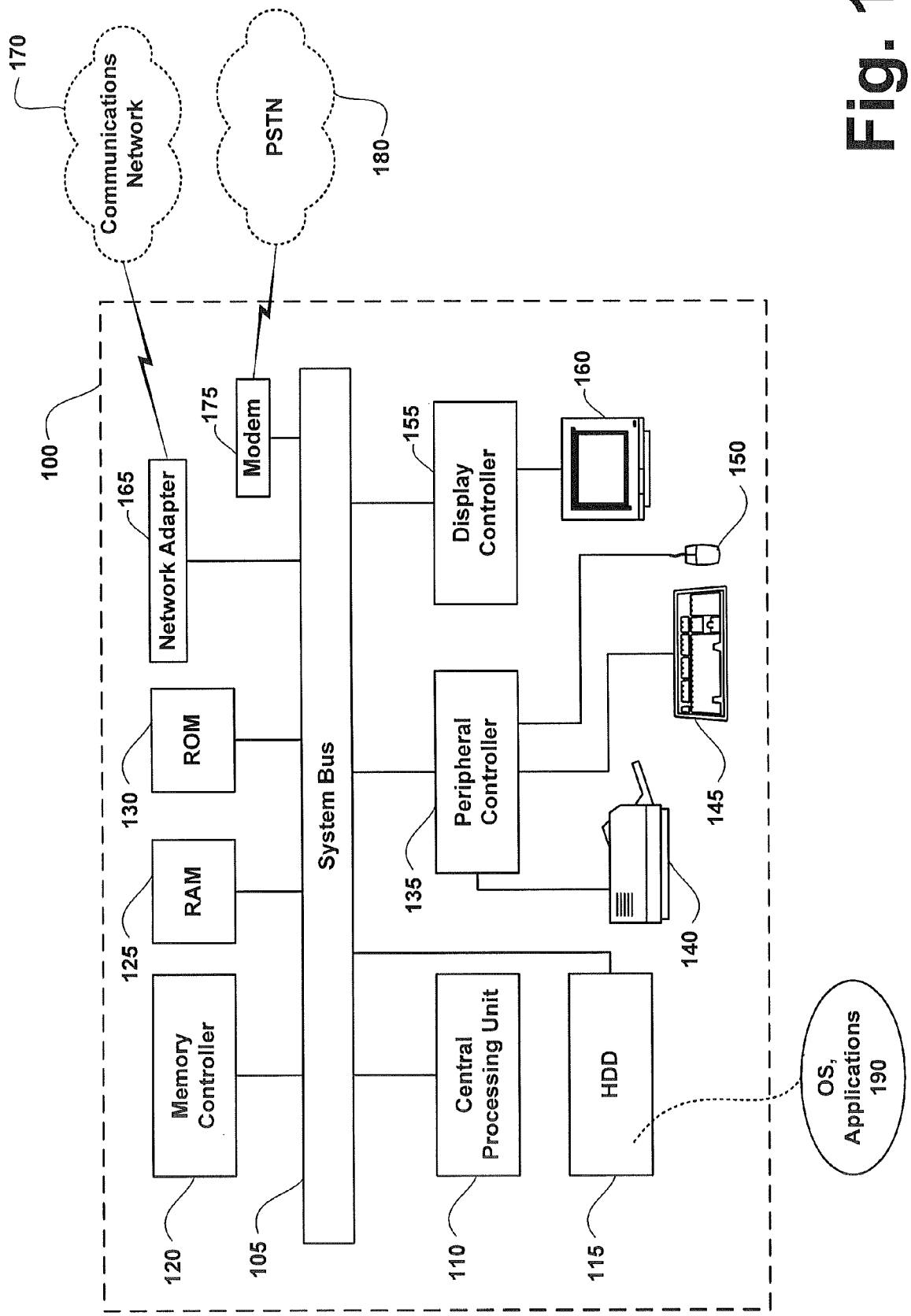
FIG. 1 is a block diagram of an exemplary computing system for use in accordance with herein described systems and methods.

FIG. 1 is a schematic diagram depicting an exemplary computing system 100 for use in accordance with herein described apparatus, system and method. Computing system 100 is capable of executing software, such as an operating system (OS) and a variety of computing applications 190, including thick and thin client applications, by way of non-limiting example. Such applications may include, by way of non-limiting example, the fitness application(s) discussed herein.

The operation of exemplary computing system 100 is controlled primarily by computer readable instructions, such as instructions stored in a non-transitory manner on a computer readable storage medium, such as hard disk drive (HDD) 115, optical disk (not shown) such as a CD or DVD, solid state drive (not shown) such as a USB "thumb drive," a remote server or servers (not shown), or the like. Such instructions may be executed within central processing unit (CPU) 12 to cause computing system 100 to perform operations. Thereby, the CPU 12 may access or execute computing code instructions from storage medium 115 to collectively provide the engine(s) that provide the systems and methods discussed hereinthroughout.

It is appreciated that, although exemplary computing system 100 is shown to comprise a single CPU 12, such description is merely illustrative as computing system 100 may comprise a plurality of CPUs 12. Additionally, computing system 100 may exploit the resources of remote CPUs (not shown), for example, through communications network 170 or some other data communications means.

In operation, CPU 12 fetches, decodes, and executes instructions from a computer readable storage medium such as HDD 115. Such instructions can be included in software such as an operating system (OS), executable programs, and the like. Information, such as computer instructions and other computer readable data, is transferred between components of computing system 100 via the system's main data-transfer path. The main data-transfer path may use a system bus architecture 105, although other computer architectures (not shown) can be used.

Memory devices coupled to system bus 105 can include random access memory (RAM) 125 and read only memory (ROM) 130. Such memories include circuitry that allows information, such as the databases, relational databases, and the like discussed hereinthroughout, to be stored and retrieved. ROMs 130 generally contain stored data that cannot be modified. Data stored in RAM 125 can be read or changed by CPU 12 or other hardware devices.

Display 160, which is controlled by display controller 155, can be used to display visual output and/or presentation generated by or at the request of computing system 100. Such visual output may include text, graphics, animated graphics, and/or video, for example. Display 160 may be implemented with a CRT-based video display, an LCD-based flat-panel display, gas plasma-based flat-panel display, touch-panel, or the like. Display controller 155 includes electronic components required to generate a video signal that is sent to display 160.

Further, computing system 100 may contain network adapter 165 which may be used to couple computing system 100 to an external communication network 170, which may include or provide access to the Internet and/or the aforementioned remote servers and/or the aforementioned storage devices. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

It is appreciated that exemplary computing system 100 is merely illustrative of a computing environment in which the herein described systems and methods may operate. Thus, the exemplary system discussed does not limit the implementation of the herein described systems and methods in computing environments having differing components and configurations, as the inventive concepts described herein may be implemented in various computing environments using various components and configurations.

Figure 2:
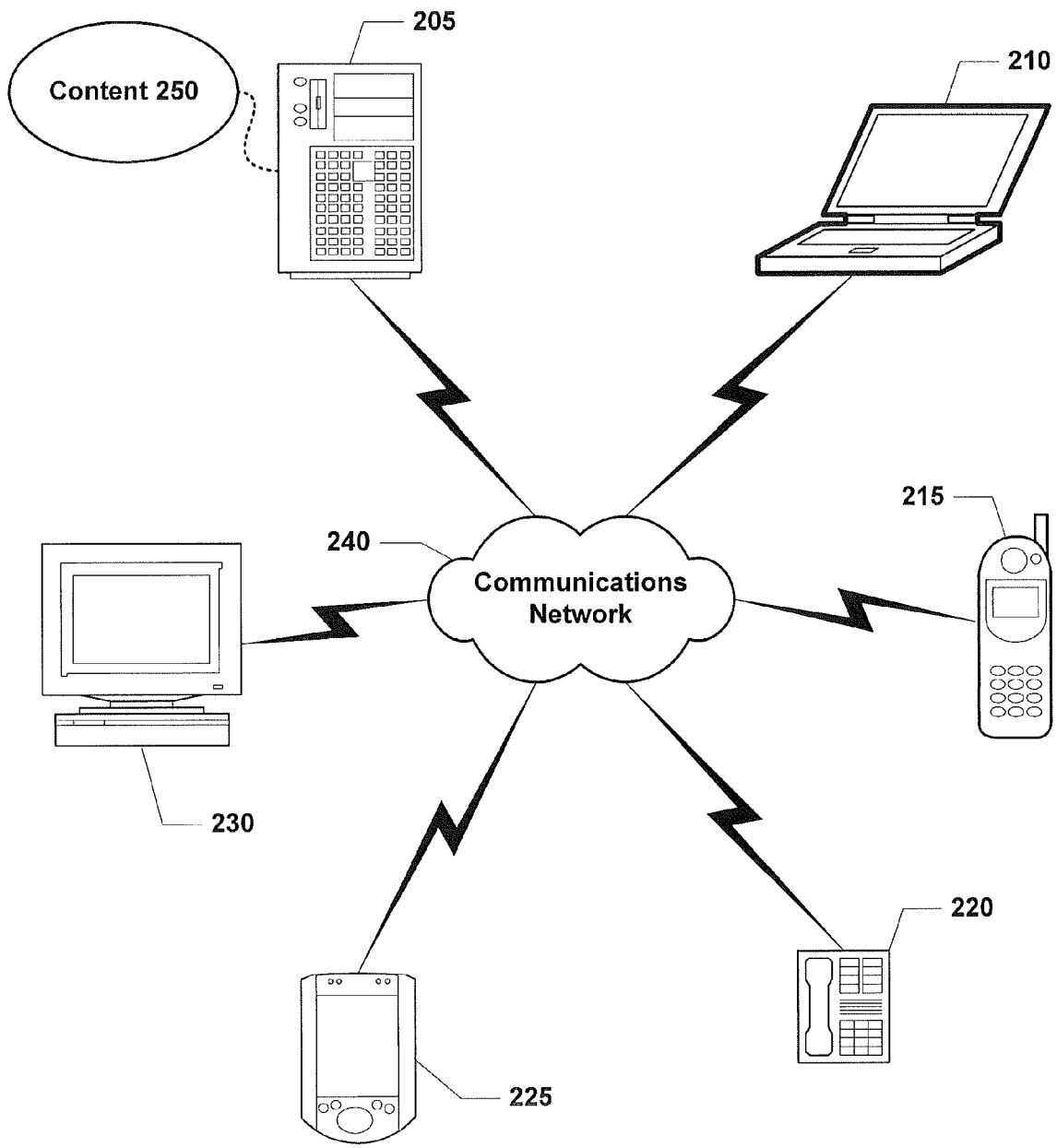
FIG. 2 is a block diagram showing an exemplary networked computing environment for use in accordance with herein described systems and methods.

As shown in FIG. 2, computing system 100 may be deployed in networked computing environment 14. In general, the above description for computing system 100 applies to server, client, and peer computers deployed in a networked environment, such as, for example, server or remote computer 16, tablet/laptop/mobile computer with CPU 12, and desktop computer with CPU 12. FIG. 2 illustrates an exemplary illustrative networked computing environment 14, with a server in communication with client computing and/or communicating devices via a communications network, in which the herein described apparatus and methods may be employed.

As shown in FIG. 2, server 16 may be interconnected via a communications network 14 (which may include any of, or any combination of, a fixed-wire or wireless LAN, WAN, intranet, extranet, peer-to-peer network, virtual private network, the Internet, or other communications network such as POTS, ISDN, VoIP, PSTN, etc.) with a number of client computing/communication devices. Servers and network connected CPUs may comprise dedicated machines operable to process and communicate data such as digital content to and from client devices using any of a number of known protocols, such as hypertext transfer protocol (HTTP), file transfer protocol (FTP), simple object access protocol (SOAP), wireless application protocol (WAP), or the like. Additionally, networked computing environment 14 may utilize various data security protocols such as secured socket layer (SSL), pretty good privacy (PGP), virtual private network (VPN) security, or the like. Each client or other device 12, 16 may be equipped with an operating system operable to support one or more computing and/or communication applications, such as a web browser (not shown), email (not shown), or the like, to interact with a server.

Referring now to FIG. 3A, a sample eligibility file from a company with pre-defined sets of groups is shown. The administrators have computers 12 that are connected through a network 14 to a remote system computer 16. The network 14 can be private, but is expected to be connected to the Internet.

Referring to FIG. 3B, a segment of a traditional office 10 is shown in which employees work. The employees have computers 12 that are connected through a network 14 to a remote system computer 16.

Each employee is provided with a monitoring unit 20. The monitoring unit 20 is worn on the body of the employee. Preferably, the monitoring unit 20 is connected to the shoe 22 of the employee. However, the monitoring unit 20 can also be connected to a sock, watchstrap, belt, or other such feature on a limb or waist of the employee. As will later be explained in more detail, the monitoring unit 20 records data corresponding to forces experienced by the monitoring unit 20 in a given time period. The data can be used to determine whether or not exercise has occurred. The data can also be used to determine the type of exercise performed and when that exercise was performed.

In the office 10, at least one transceiver 24 is installed. The transceiver 24 transmits an activation signal 26 that is received by any monitoring unit 20 within range. Once a monitoring unit 20 receives an activation signal 26, it transmits its stored data to the transceiver 24 along with an identifier code for the employee. The transceiver 24 receives both the identifier code and the transmitted data. That information is then forwarded to the remote system computer 16 via the same computer network 14.

The downloading of data from the monitoring unit 20 to the system computer 16 happens automatically each time an employee comes into the office 10. As such, the data transfer is passive, needing no effort from the employee. The employee need only remember to connect the monitoring unit 20 to a shoe or similar article of clothing being worn.

The system computer 16 utilizes the data from each employee to track what exercise has been performed by the employee and when. Many types of exercise can be identified by the system computer 16 through analysis of the type of data that is received. For instance, walking and running are easily identifiable. Other types of exercise can be identified as exercise, but the specific exercise may not be discernable. For instance, the data produced from cycling on flat ground is nearly identical to the data produced while cycling up a steep hill. However, riding up the steep hill burns more calories than riding on the flat surface.

When an employee logs onto his/her office computer 12, the employee may be actively prompted with a message that indicates the exercise system has received new data. Otherwise, the system may be passive and wait for an employee to log onto the exercise system. Once interacting with the exercise system, the employee can recall data in many formats to show when exercise was performed, what exercise was performed, and for how long. As will later be explained, the data can also be applied to selected exercise challenges and competitions.

If the exercise system has received data that it cannot positively identify, then the employee is prompted to identify the exercise. The employee is reminded of when the exercise was performed and for how long. The employee then is provided with a list of exercises from which to choose. The employee selects the exercise that best described the activity performed. The system computer 16 then has a complete set of data corresponding to the exercise activities of the employee.

Figure 6:
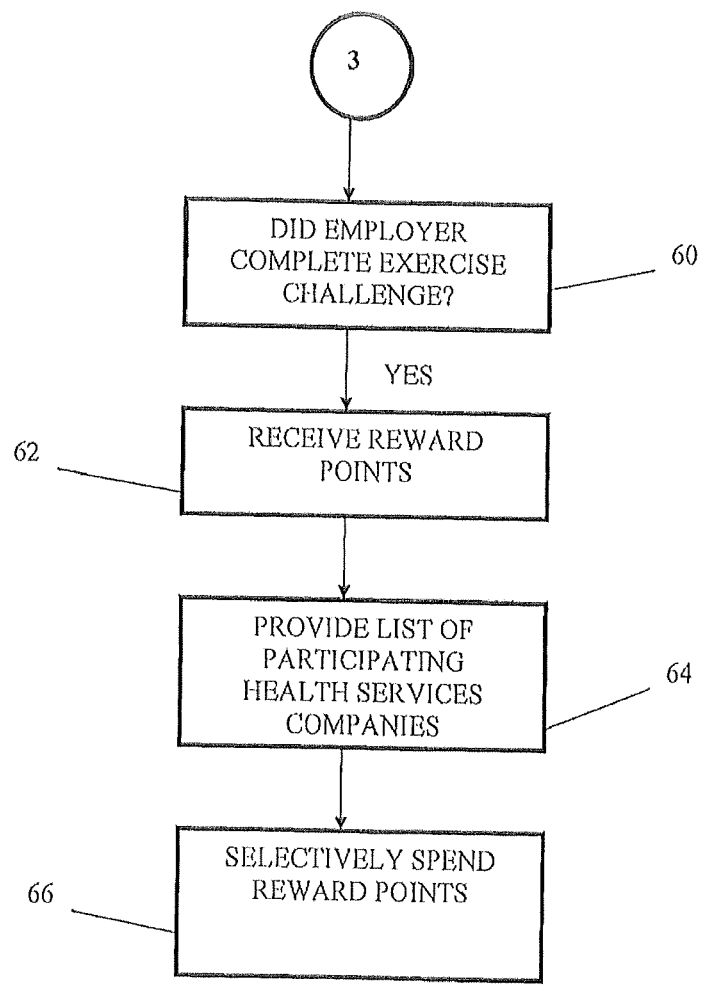
FIG. 6 is a block diagram showing a methodology of reward in accordance with the present invention system.

To help motivate the employee, the exercise system 10 allows an administrator to manipulate the groupings imported in FIG. 6 to easily create and present individual and team challenges and competitions to the employee. In the case of teams the system automatically normalizes the challenges based on number of participants. The system computer 16 then applies all exercise data to those challenges and competitions, in a manner later explained. As used herein, challenges may mean any task which may be completed by a participant as an individual compared to other individuals, or as a part of a group as compared to other individuals or groups, and may include, for example, walking, running, climbing stairs, swimming, water aerobics, riding a bicycle, using gym equipment, playing an organized game, such as basketball, for example, dancing, yoga, stretching, and playing video games requiring physical commotion.

Figure 4:
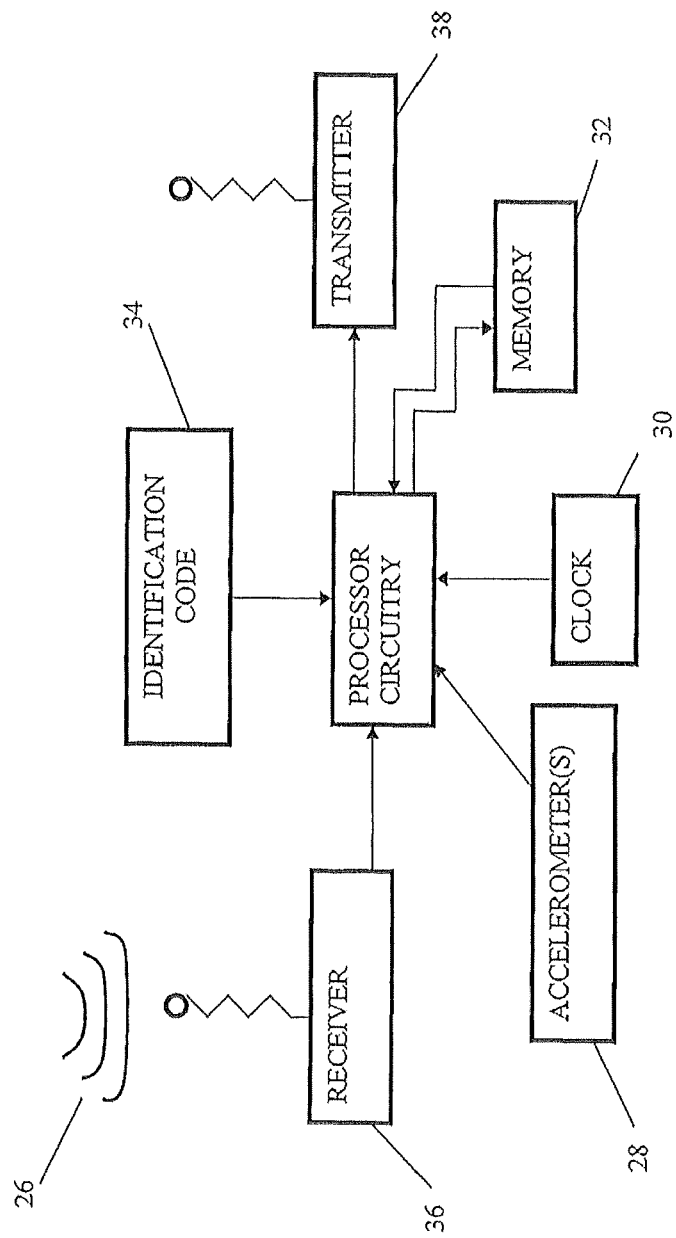
FIG. 4 is a schematic of an exemplary embodiment of a monitoring unit.

Referring to FIG. 4, a schematic of a monitoring unit 20 is shown. Each monitoring unit 20 contains at least one accelerometer 28. The accelerometers 28 are preferably microelectromechanical systems (MEMS), however other technologies can be used. The accelerometers 28 measure changes in acceleration in different orientation planes and convert that information into corresponding electronic signals. Within the monitoring unit 20, a clock 30 is provided. The clock 30 creates a time code signal that is coupled to each electronic signal produced by the accelerometers 28. The combined signals are stored in a memory 32 as data signals.

Each monitoring unit 20 has its own identification code 34 that identifies the monitoring unit 20. Each monitoring unit 20 also has a receiver 36 for receiving the activation signal (26, FIG. 1) and a transmitter 38 for transmitting both the data signals and the identification code 34. Suitable monitoring units 20 that can be adapted for use by this invention are manufactured by Fitlinxx, Inc. of Norwalk, Conn.

Figure 5:
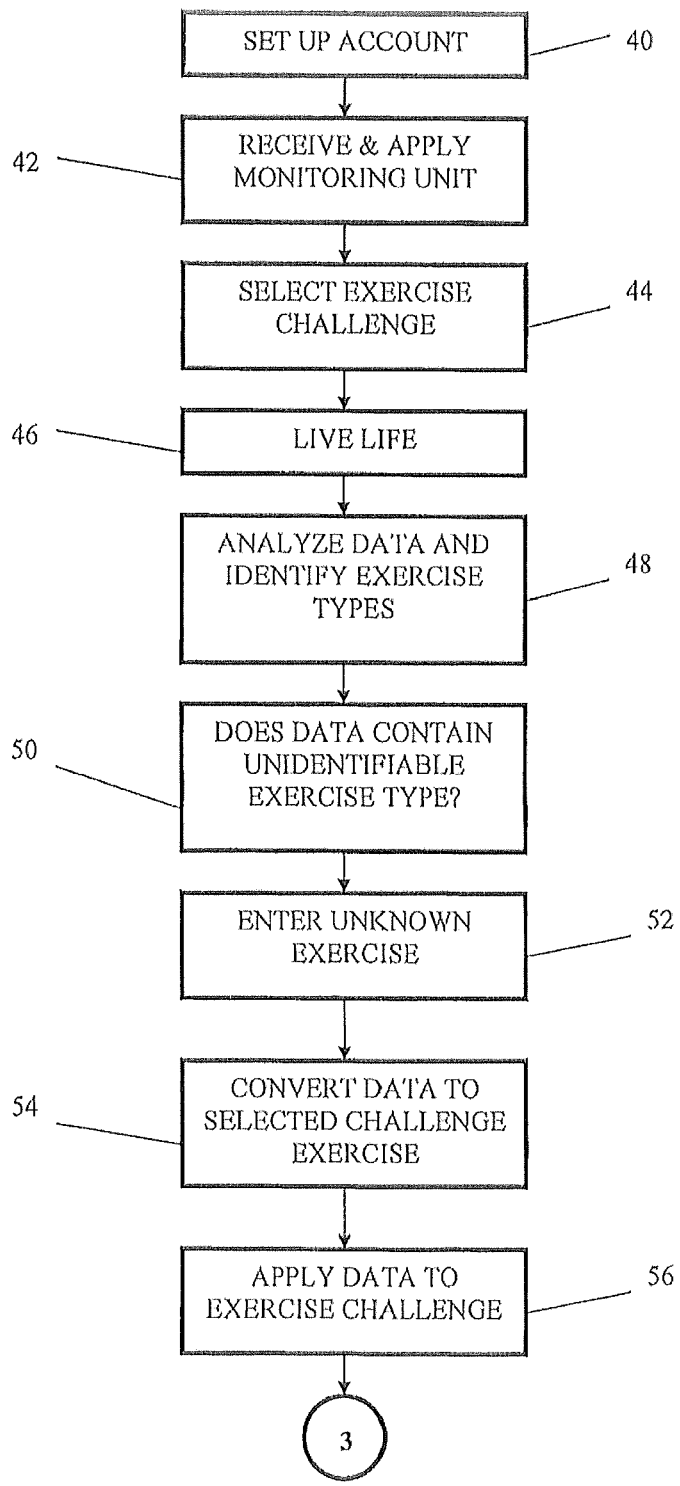
FIG. 5 is a block diagram showing a methodology of operation for the present invention system.

Referring now to FIG. 5 in conjunction with FIG. 3B, the operational methodology of the system is described. As is indicated by Block 40, each participating employee is assigned an account number for accessing the system computer 16. Furthermore, each participating employees is provided with at least one monitoring unit 20. See Block 42. An employee may be given more than one monitoring unit 20. In this manner, the employee can attach a monitoring unit 20 to each of the sets of shoes he/she commonly wears. Within the system computer 16, the identification code 34 for each monitoring unit 20 given to an employee is assigned to the account for that employee.

Once an employee has set up an account, the employee is provided with a choice of exercise challenges from which to choose. See Block 44. For instance, one challenge may be a virtual hike. An employee, using their network computer 12, may select a geographical area, such as Pennsylvania, France, Kenya or the like. The systems computer 16 will then generate a virtual hiking tour. The systems computer 16 will then indicate how many steps are required to complete the virtual tour. For example, it may be 456,789 steps. The challenge, then, becomes for the employee to walk 456,789 steps. Each time the employee downloads data to the system computer 16, the data is converted to steps, if necessary, and applied to the challenge. The systems computer 16 may provide different images of different landmarks in the selected geographical area as data is applied to the challenge.

In addition to counting physical movement, the present invention may also record a participant's time spent in activity and may base all or a portion of the reward points or other completion credit based on the time spent. For example, a person who may be in less than ideal physical condition and/or is injured, may participate in the virtual hike, as described above, but may only complete half as many steps as most participants do in the same period of time. Thus, the administrator may award such a participant the same credit that a person walking the full amount of steps would earn. Likewise, a participant who simply walks around while watching television at home may be rewarded some rewards points, for example, for the time spent in active motion.

Figure 7:
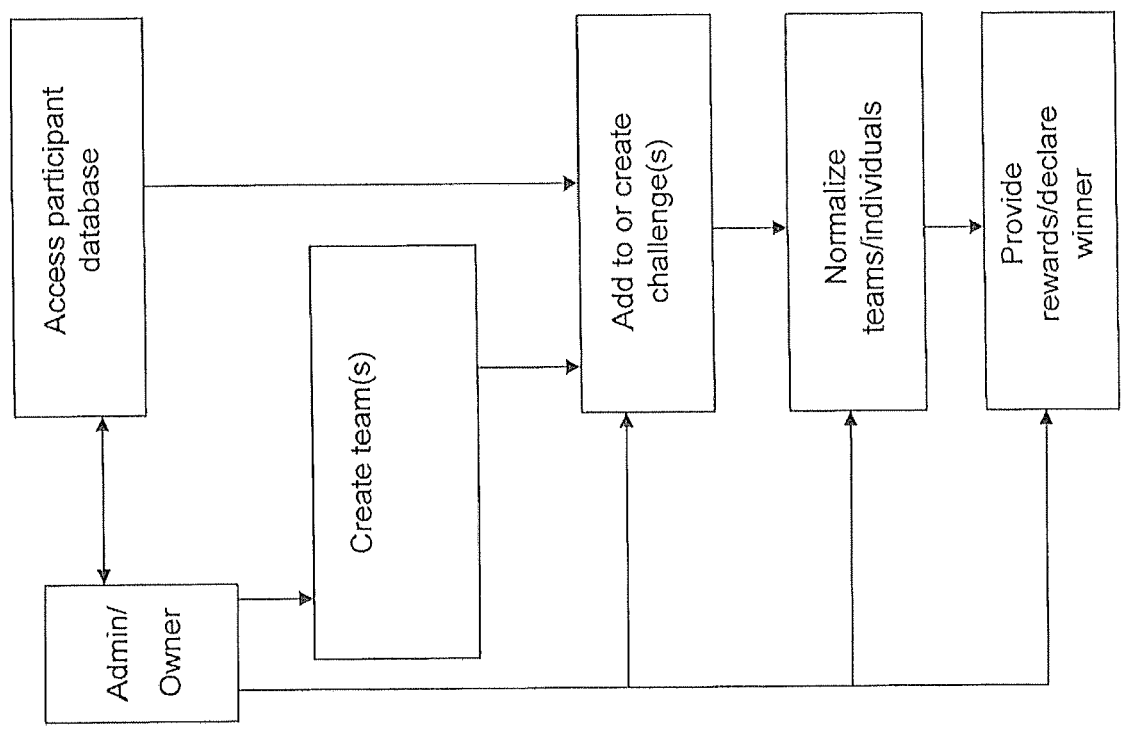
FIG. 7 is a block diagram showing the methodology of turning a multitude of groups into teams in accordance with the present invention system.

In addition to the individual challenges described, the administrator of the program may also set up team challenges. Administrators may have special access on systems computer 16 that may allow them to take the groups imported from FIG. 7 and turn those groups into teams. The administrator can create a multitude of challenges and competitions between these teams. By way of non-limiting example, an administrator may implement achievement challenges, top performance team competitions, and most improved competitions. In such exemplary instances, an achievement challenge may indicate the obtaining of a particular goal, such as a goal of a team-aggregate number of steps; a top performance competition may reward the team that achieves at a higher level than other teams, such as a team that aggregates more steps than other teams; and a most-improved competition may indicate a reward or a "victory" to the team that, either as individuals or in the aggregate, improved performance in a current challenge over the performance recorded in a previous challenge by the largest amount, such as by the highest number of steps. Teams may also be normalized by number of participants, such as by averaging, for example, thereby allowing large and small groups to compete with each other.

Other challenges may also be provided. For example, one employee may enter into direct competition with other employees to complete a stated amount of steps in a stated amount of time. Rewards may be provided to people who accomplish or win challenges. The nature of the rewards is later described in conjunction with FIG. 6.

As is indicated by Block 46, once an employee is entered into a challenge, the system automatically tracks the steps being accumulated. It is hoped that the presence of the challenge, the encouragement of teammates, and a potential reward or completing the challenge will entice the employee to exercise wherever and whenever they can. For instance, an employee may park farther away from work in order to walk a little more. The employee may take the stairs instead of the elevator. All of these little bouts of physical activity are automatically recorded and are applied toward the employees challenge.

The exercise data generated by an employee is stored until the employee transfers data to the system computer 16. This can be done automatically by having the employee come within range of an office transceiver 24. However, if desired, an employee can connect a transceiver directly to a computer at their home or office, using a standard USB port. This is very useful for people who 13 work some days at home or travel often as part of their job. Once the exercise data is downloaded, the data is analyzed by the system computer 16. See Block 48. First, the data is identified according to the types of exercise preformed the data. Different exercises produce different types of data. Since the monitoring unit 20 contains accelerometers, the data gathered is analog in nature. Walking produces specific signals within the accelerometers at repeating intervals. A walking signal is straightforward to identify. Running creates greater accelerometer signals at faster intervals and is easy to identify. The signal profiles of numerous exercises are known. For instance, the signals generated by bicycle riding, swimming, and climbing stairs are readily identified. However, the signals generated by some other exercises can be identified as exercise, but cannot be precisely identified as to the type of exercise. For example, tennis and dodge ball create nearly identical signals from a monitor unit 20 worn on the foot.

As is indicated by Block 50 and Block 52, when a signal contains exercise data that cannot be specifically identified, the system computer 16 prompts the employee the next time the user logs onto the system. In the prompt, the employee is provided with a choice of exercises from which to choose. The employee is reminded of when the exercise occurred and for how long the exercise lasted. The user then selects the exercise that best fits the exercise that was recorded.

In some circumstances, the monitoring unit 20 may fail to recognize some exercise that has occurred. For instance, if an employee is wearing the monitoring unit on their foot and then goes canoeing, the monitoring unit 20 many not record any exercise even though strenuous exercise is occurring. In such situations, an employee does have the option of manually entering a specific exercise for a specific period of time. However, the exercise selected cannot be contrary to the data signals received for that period. If the selected exercise does not match the data signal, it may be assumed that the employee is lying or exaggerating and the data signal may be ignored by the system computer 16.

Once the system computer 16 has all the exercise data for a specific period of time, the system computer 16 converts the exercise data to steps. See Block 54. For example, if walking is assigned a caloric expenditure of 250 calories per 2,000 steps, then swimming for fifteen minutes is converted to 2,000 steps. This is because swimming for fifteen minutes also burns 250 calories, which is a caloric equivalent of 2,000 steps.

Once all the exercise data is converted into its challenge exercise equivalent, then the data is applied to the selected challenge. See Block 56. Accordingly, an employee who rides a bicycle to work and plays basketball, may quickly complete a walking challenge without ever intentionally walking for exercise.

By converting all recorded exercise data into its challenge exercise equivalency, all employees can compete toward the same goal even though they exercise in different ways. Also, various employees can compete directly with each other, even though each employee exercises in a different way.

Referring to FIG. 6, the rewards portion of the method of operation can be outlined. As has been previously stated, an employee selects a challenge in which to participate. An employer may elect to provide rewards to the employee if the challenge is met. The rewards may be financial or work related, such as an extra vacation day. However, a unique rewards program is preferred.

As is indicated by Block 60 and Block 62, if an employee successfully completes an exercise challenge, then the employee is assigned a number of virtual reward points to his/her account. The number of reward points to be granted is directly dependent upon the difficulty of the exercise challenge that has been completed.

The administrator of the present invention system may enter into contracts with a variety of health promoting venues. The venues may include health clubs, sports clubs, sports equipment retails, vitamin retails, and the like. In these contracts, the venue companies agree to accept the virtual points awarded employees in exchange for some predetermined compensation. A list of participating companies is provided to each employee. See Block 64. The employee can then spend his/her reward points by buying the goods or services from the various participating companies. See Block 66.

By restricting the venues in which the reward points can be spent, each employee is provided a significant but limited choice. However, all the choices are beneficial to the health and well-being of the employee. It is therefore hoped that an employee's exercise will be self-perpetuating. That is, an employee earns reward points by exercising in a gym and the reward points help pay for membership in that gym. Otherwise, an employee earns reward points by playing a sport and the reward points pay for the equipment used to play that sport.

Figure 8:
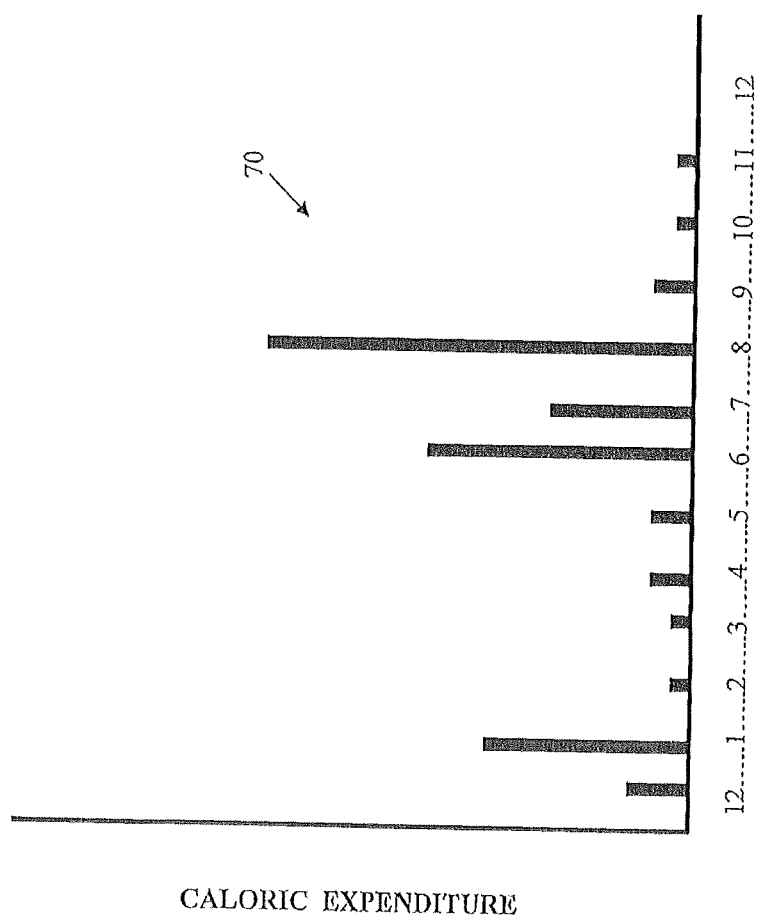
FIG. 8 is a graph plotting equivalent steps taken against time for various detected exercises.

After an employee uses the present invention system for a period of time, a great deal of information is gathered concerning when and how a particular employee exercises. This information is formatted and provided to the employee for the benefit of the employee. Referring to FIG. 8, a graph 70 is shown that shows activities plotted by time and calories burned during the course of one day. The graph 70 shows only one of many ways the data can be formatted. However, when formatted as illustrated, an employee can see when they are exercising the most and when they are exercising the least. This may encourage employees to take the stairs or otherwise do some exercise during non-traditional hours.

Figure 9:
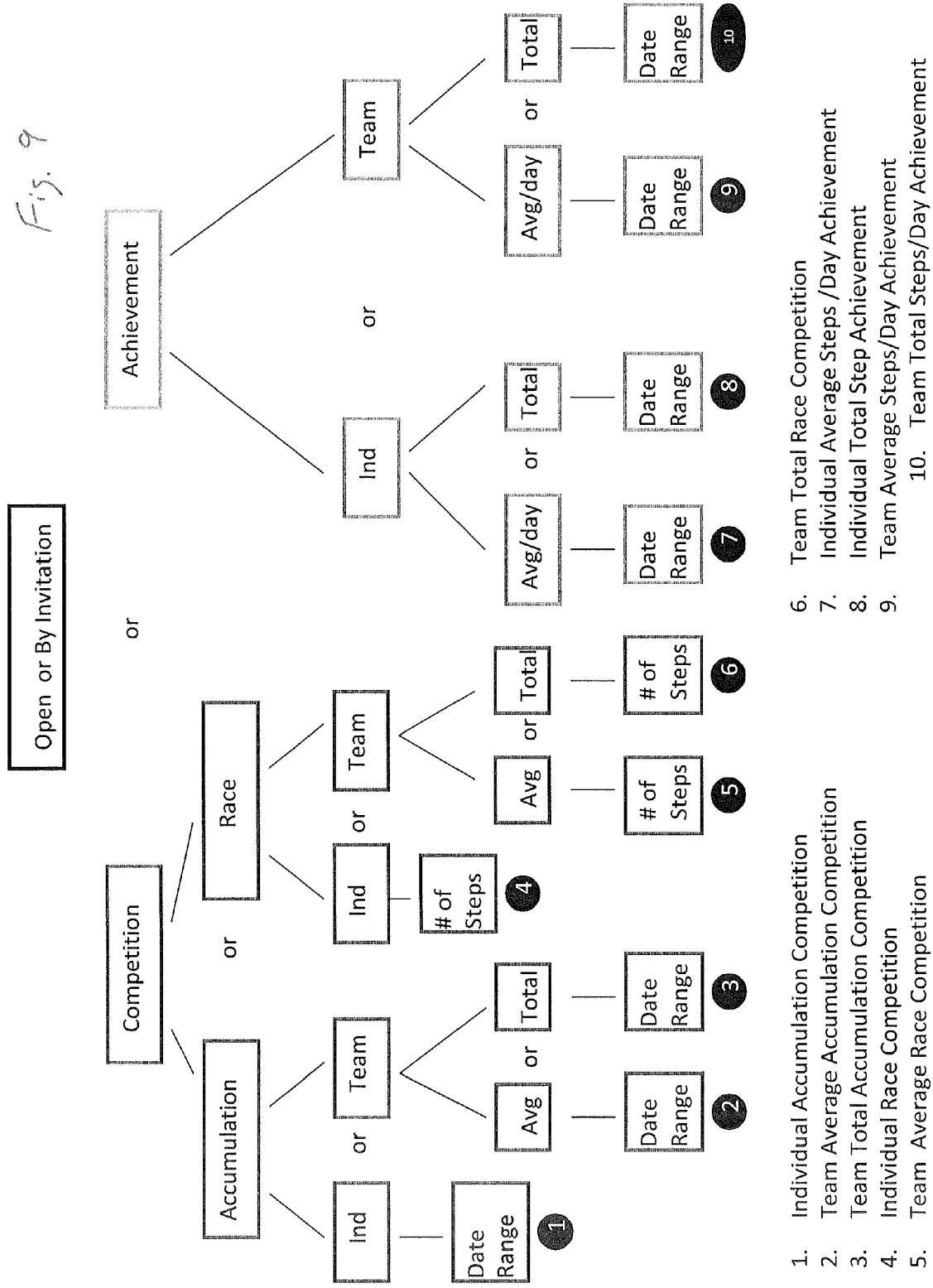
FIG. 9 is a block diagram showing an aspect of the present invention.

As discussed herein, challenges may be competition or achievement based, for example. As illustrated in FIG. 9, each type of challenge may have associated therewith a subset of categories and or attributes. For example, a competition between two teams may be based on the accumulation of reward points, or on completion of a predetermined amount of progress through a particular challenge. As discussed in more detail herein below, users of the present invention may participate freely in any number of challenges which may differ in both measurement and activity, and/or may be limited in an allowable number of challenges, such as based on administrator choice, health limitations, or the like.

For example, the present invention may allow a company administrator to create any number of challenges for individual and/or team participants as well as for intra-company and inter-company competitions. As discussed herein below, rules may be assigned to each challenge such that scoring and/or performance measures may be altered to fit any situation known to those skilled in the art. For example, an administrator may set parameters for which a team of participants "wins" are particular challenge by setting up a goal of reward points which may be earned over a period of time without exceeding a maximum per day progression through a challenge. For example, a walking challenge between two teams may be held over a one month period with each team only able to collect reward points on a maximum of the equivalence of three (3) miles walked per day.

Similarly, a winning team maybe declared based on the average distance walked over a defined period of time. In this way, teams and/or team participants, who may not be able to contribute to the walking total during one week while able to contribute more a second week, for example, may not so prejudice the team's average so as to disincentivise themselves or the team as a whole. Thus, an administrator may control the rules to effect participation by target participants and may alter the rules to achieve an initial participation level of at least fifty-percent (50%) of target participants. An administrator may further control the rules to effect participation by the initial participants over a period of time, such as a participation retention rate of at least seventy-five-percent (75%).

In addition to rules controlling outcomes, the administrator may also construct competitive challenges between community members and/or those outside a particular community. For example, a competitive challenge may be constructed between two participants and/or against the participant themselves. Further, a competitive challenge may be constructed to allow a participant in the New York City office of a corporation to compete against a participant in the Philadelphia office of the same corporation. Similarly, teams from different locations may compete against each other and may further compete against unrelated organizations. For example, company A may participate in a challenge against company B. The present invention may also allow participants to view how other participants/teams are performing with regard to at least one challenge or competition. In this way, motivation for exercise may be found without directly competing against another participant and/or team.

The present invention may also provide at least one rules engine for the creation of team(s) and/or challenge(s) within an organization, such as based on at least one information file provided by the organization. The file provided by the organization may, for example, contain information about a set of users associated with the organization such as, for example, user name, gender, age, location, weight, height, challenge preference, employment position, office and/or business location, health restriction information and the like. The file may be uploaded by an administrator at the organization, for example, and may be updated as necessary. The file may also include information regarding users from just one location, and may preferably contain information from all locations that include users associated with the organization who may wish to, or who may ask to, participate in challenges. Such information may be provided, for example, to the file by data entry at the organization, batch upload into autopopulating fields by the organization, or the like, for example. Further, it is preferable in the present invention that such information be consistent in its form and format across multiple organizations, such that the challenge engine (i.e., a rule engine) can readily access the relevant information from any organization to set up a desired challenge based on a single instruction (i.e., all sales people in Toledo, Ohio will challenge all office staff in Albany, N.Y.) or a limited set of instructions or selections, such as via drop down (i.e., select the organization, then the offices, then the personnel category to compete in a challenge).

For example, an organization may have several office locations spread through the United States—and may further categorize this locations into districts or territories. For example, three offices located in New Jersey, Connecticut, and New York, respectively, may be considered the Northeast offices, while four offices located in Atlanta, Birmingham, Charleston and Tallahassee, respectively, may be considered the Southeast offices. Similarly, an organization may have a single person in each of these cities and may consider the "offices" to be territories, for example. In any case, the users associated with the organization may be further associated with defined groups within the present invention.

In an embodiment of the present invention, the file to be uploaded may be considered an eligibility file and may preferably contain at least three categories of information in addition to user identifying information: user location, user employment position, and resident organization office. The present invention may parse such an eligibility file, such as via the rules engine, and provide the administrator, for example, with location-based challenge options.

Continuing with the example above, an eligibility file having information associated with employees at offices in New Jersey, Connecticut, New York, Atlanta, Birmingham, and Charleston, may be parsed and categorized by the present invention into at least two groups representative of location, such as, for example, the Northeast and Southwest. The users associated with an office within a group may then be associated with at least one challenge. Further, the at least one challenge may allow users in one office and/or one group compete against a different office and/or group.

In an embodiment of the present invention, a plurality of participants may be third parties and may subscribe to at least one challenge. Such a participant may further participate in a challenge remote from the location the subscription was consummated and/or from the location where progress in the challenge is recorded. For example, a healthcare provider, such as a hospital or doctor, or a retail store, such as a large box store or pharmacy, may provide the present invention to customers on a subscription basis.

For example, Walgreens® may allow a customer to subscribe and participate in at least one challenge and may further allow for the recording of data from the participant in-store or via a provided GUI accessible through the internet. More specifically, for example, Walgreens may provide a pedometer to a subscriber and may record and/or track the progression of a walking challenge entered into by the participant each time the participant enters a Walgreens with the pedometer. As would be appreciated by those skilled in the art, challenge information may be manually entered by the participant and/or collected remotely using the aforementioned GUI and/or a sensing device provided from remote use by the participant. Similarly, the pedometer or other challenge tracking device may be communicatively couple to a mobile device, such as a smart phone, for example, which may communicate challenge progress via a specialized app, SMS or other communication means.

The providers of such third party information may also include convenience stores, such as Wawa®, for example, fast food establishments, such as Subway® and Starbucks®, for example, and other outlets, such as sporting stores, for example. In additional to providing challenge participation, further information, such as customer habits, may also be collected. For example, convenience store may track a participant's visit frequency, time spent during each visit, and/or the movement of the participant within the store. The convenience store may also track and correlate item purchased by the participant. In addition to better understand the consumer, the convenience store may provide targeted ads and/or coupons, for example, to the participant through the GUI provided to the participant to access the challenge(s).

Brands may similarly offer the present invention. For example, "The Biggest Loser" television show may offer a device which may be tracked by home users and may, for example, track and record not only physical activity, but biometric information, such as, for example, weight, body temperature, heart rate and the like. As discussed above, brands may similarly provide targeted ads and/or coupons, for example, to the participant through the GUI provided to the participant to access the challenge(s).

Establishments offer exercise services, such as gyms, for example, may also use such tracking/recording means. For example, a gym, having one or more locations, may geocode a location to allow for the tracking of a participant at that particular location. Such tagging of the participant may allow the participant to register a visit at the gym location without otherwise signing in or verifying membership. Such a visit may be eligible for reward points (based on visit, time spent and/or tracked biomedical/biomechanical information), for example, and may be used in reporting to a health care provider to track the number of gym visits (which may allow for a rebate or deduction in healthcare costs to the participant). Likewise, tagging may also allow a participant to, in real-time, update any social network, such as Facebook®, for example, and "check-in" and "check-out" at a particular gym location.

Figure 10:
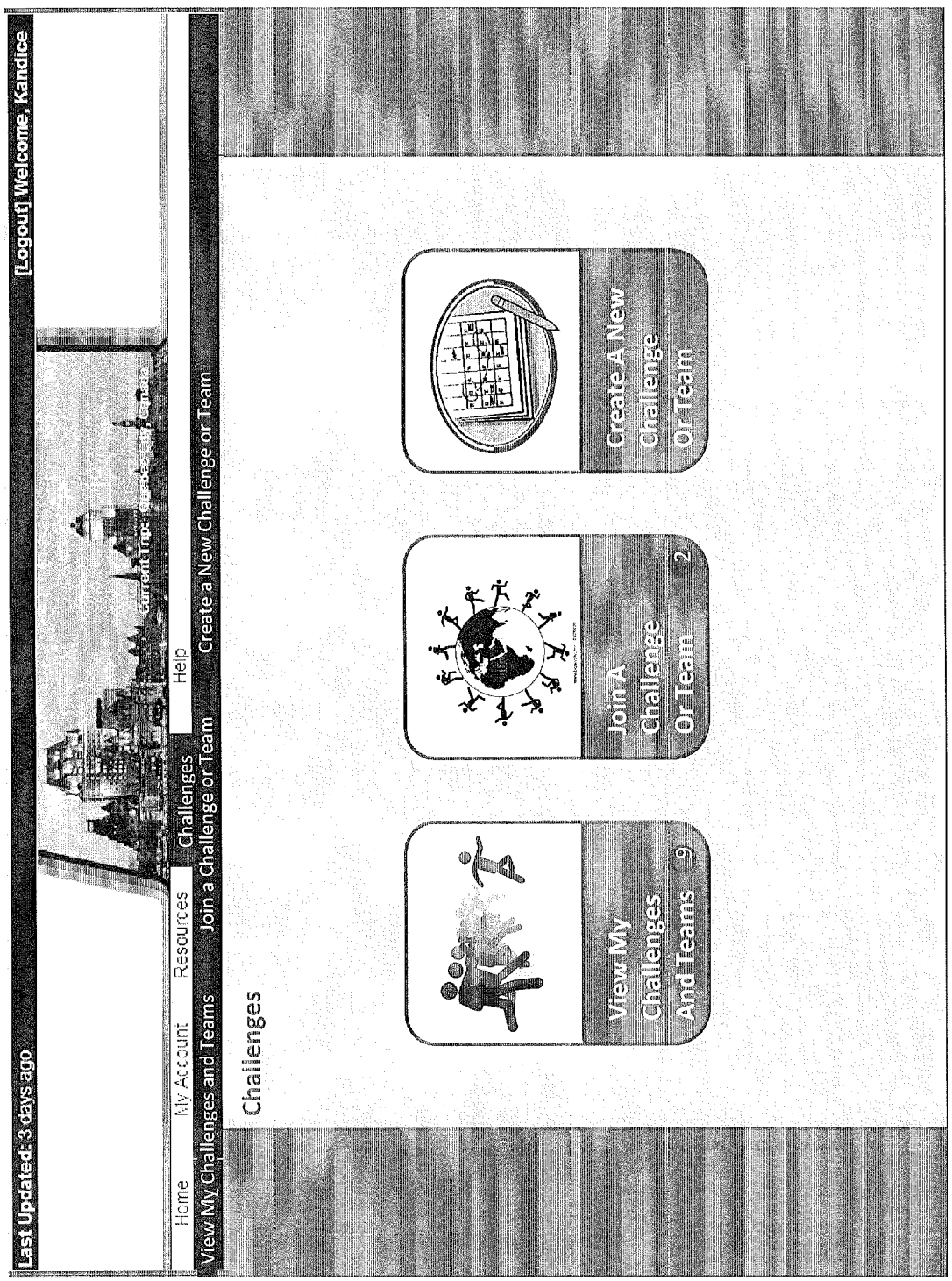
FIG. 10 is a screen shot illustrating exemplary aspects of the present invention.
Figure 20:
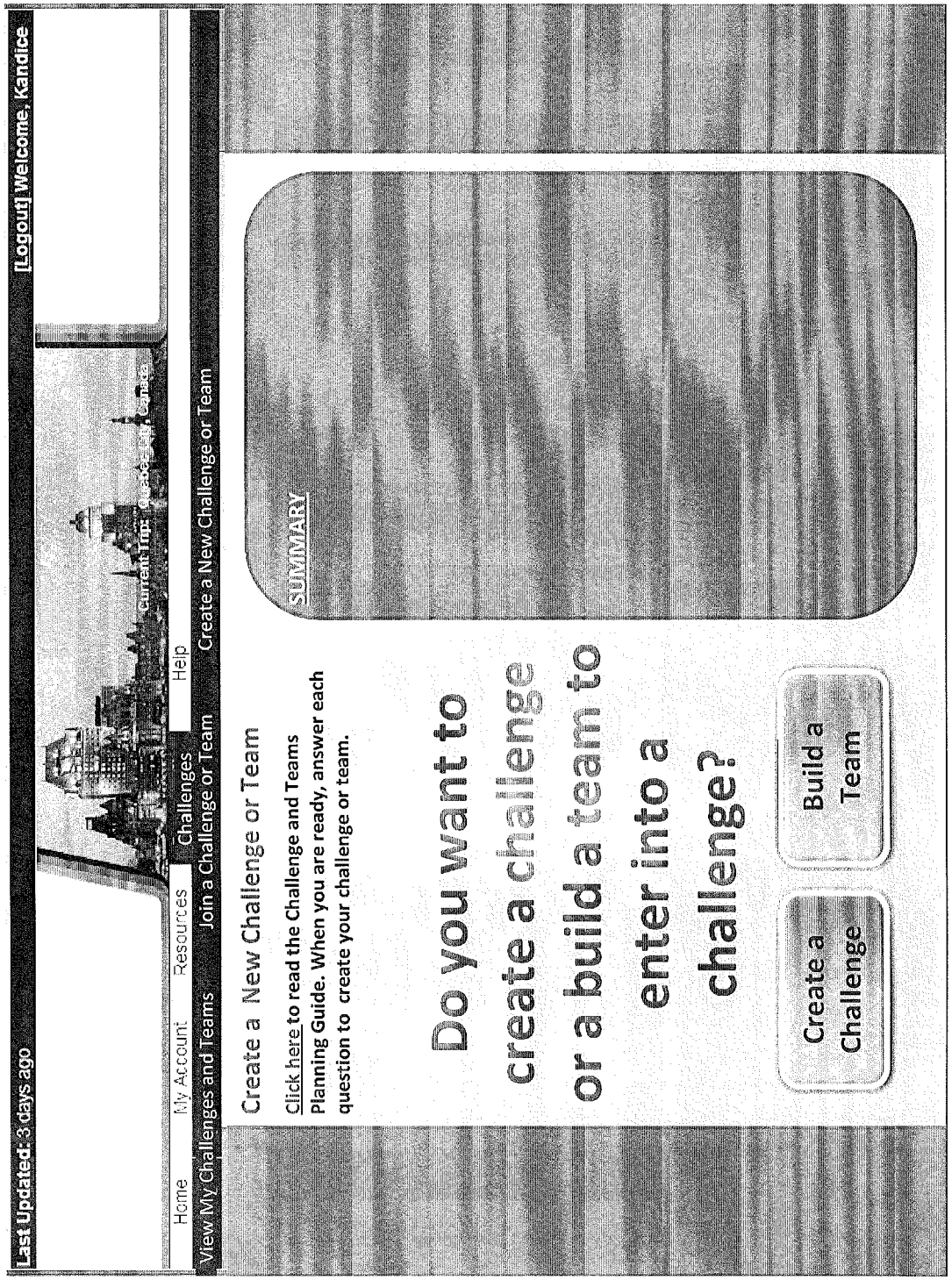
FIG. 20 is a screen shot illustrating exemplary aspects of the present invention.
Figure 21:
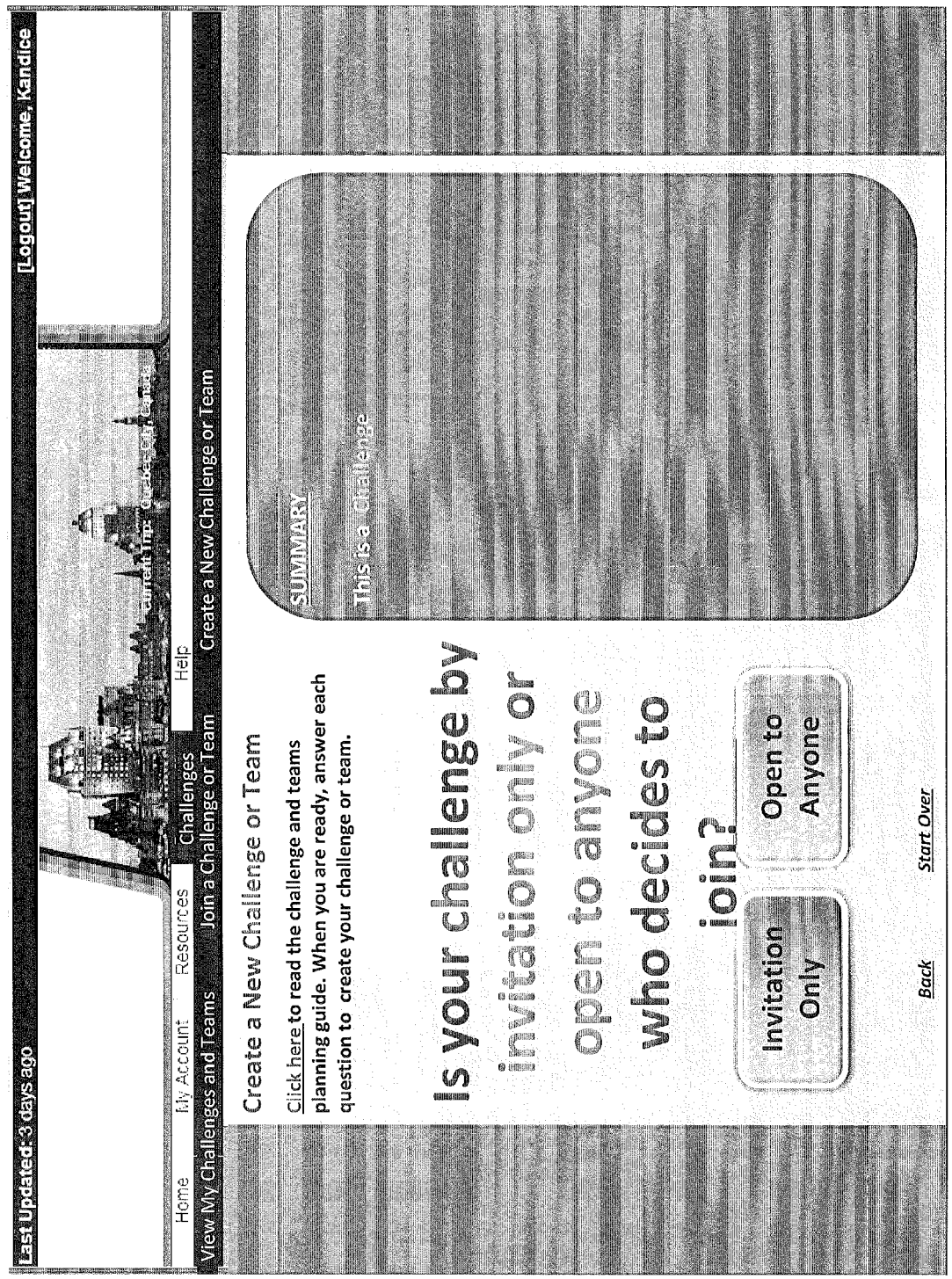
FIG. 21 is a screen shot illustrating exemplary aspects of the present invention.
Figure 22:
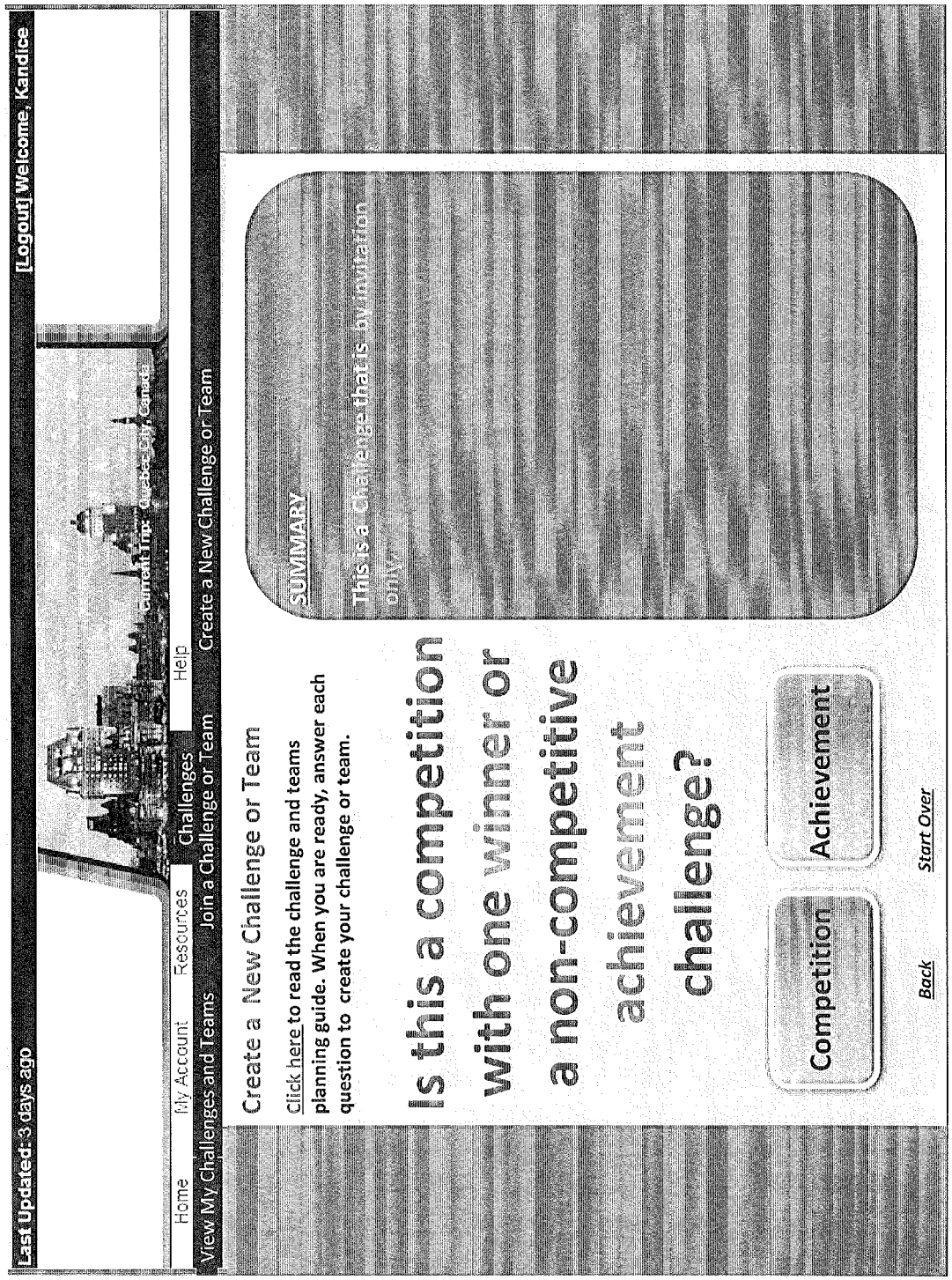
FIG. 22 is a screen shot illustrating exemplary aspects of the present invention.
Figure 23:
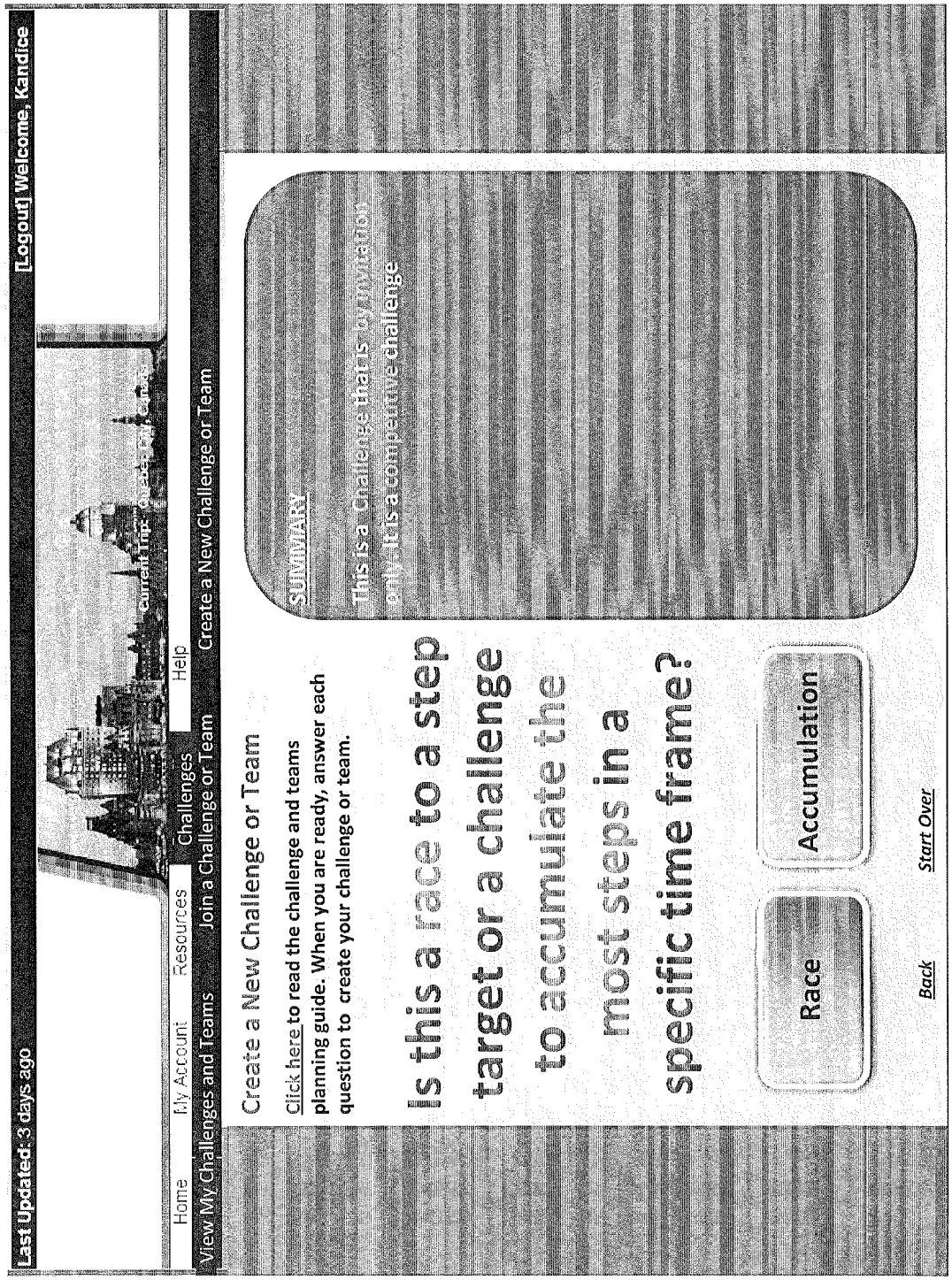
FIG. 23 is a screen shot illustrating exemplary aspects of the present invention.
Figure 2C:
Figure 29:
FIG. 29 is a screen shot illustrating exemplary aspects of the present invention.
Figure 32:
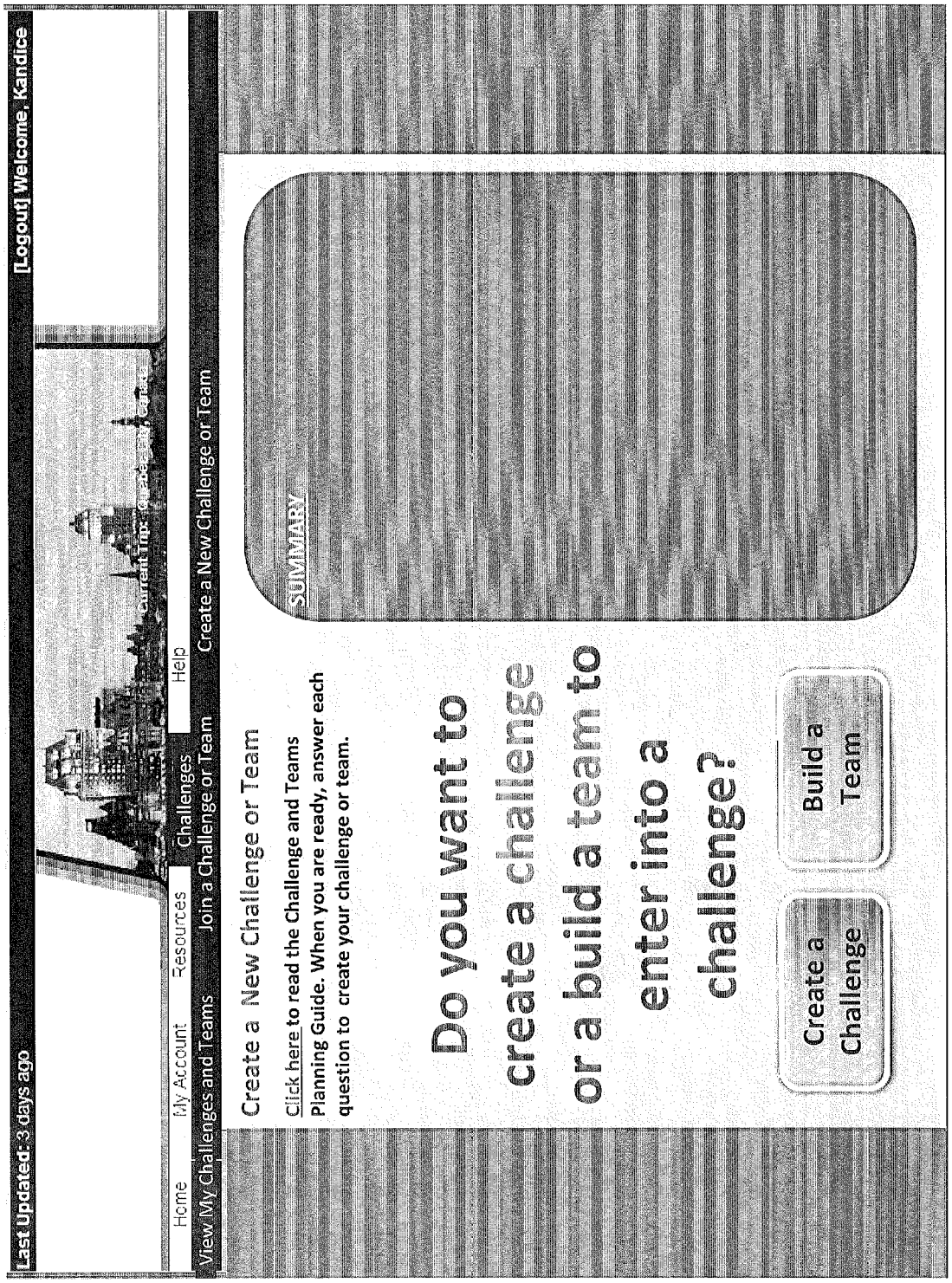
FIG. 32 is a screen shot illustrating exemplary aspects of the present invention.
Figure 33:
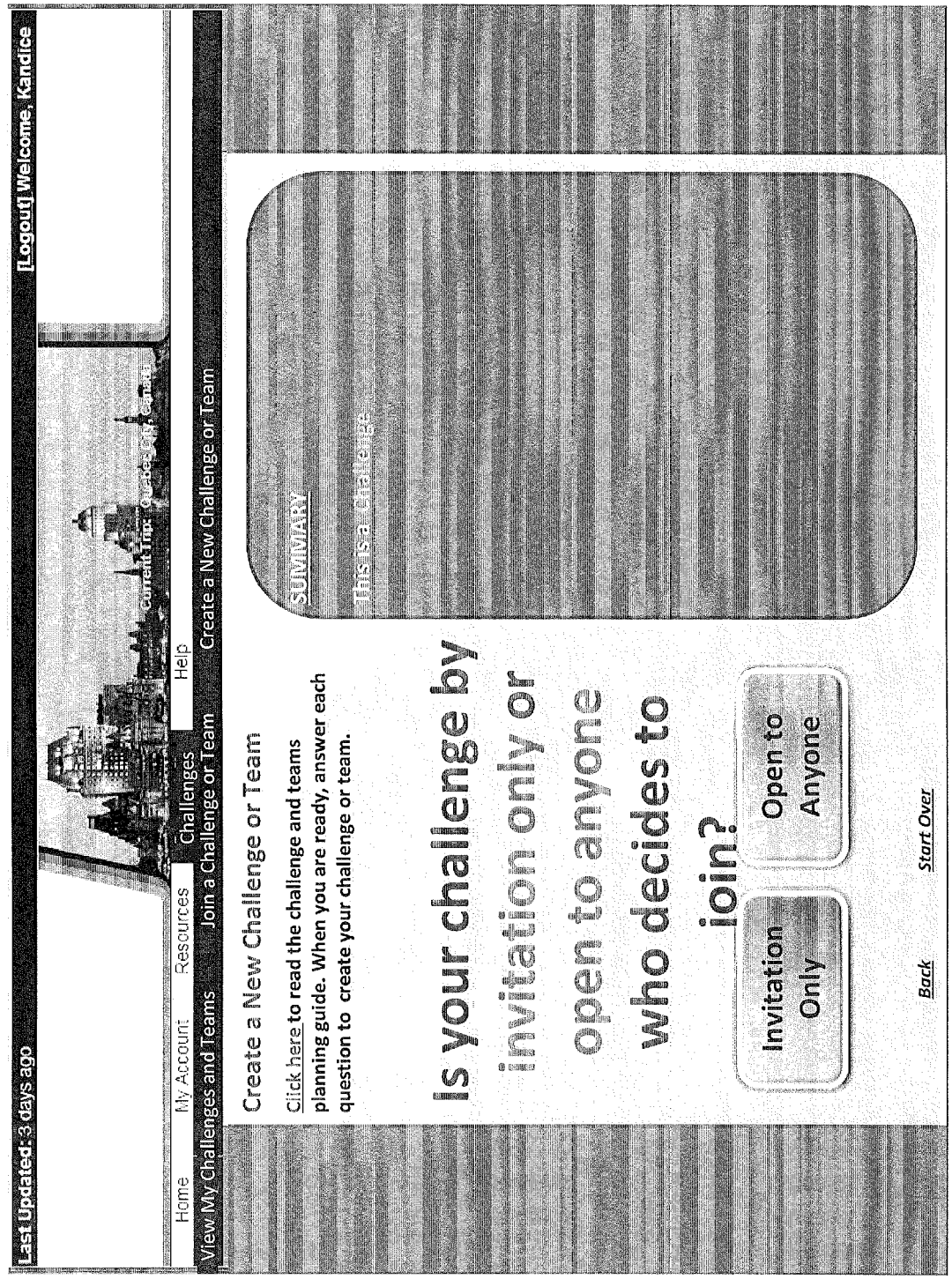
FIG. 33 is a screen shot illustrating exemplary aspects of the present invention.
Figure 34:
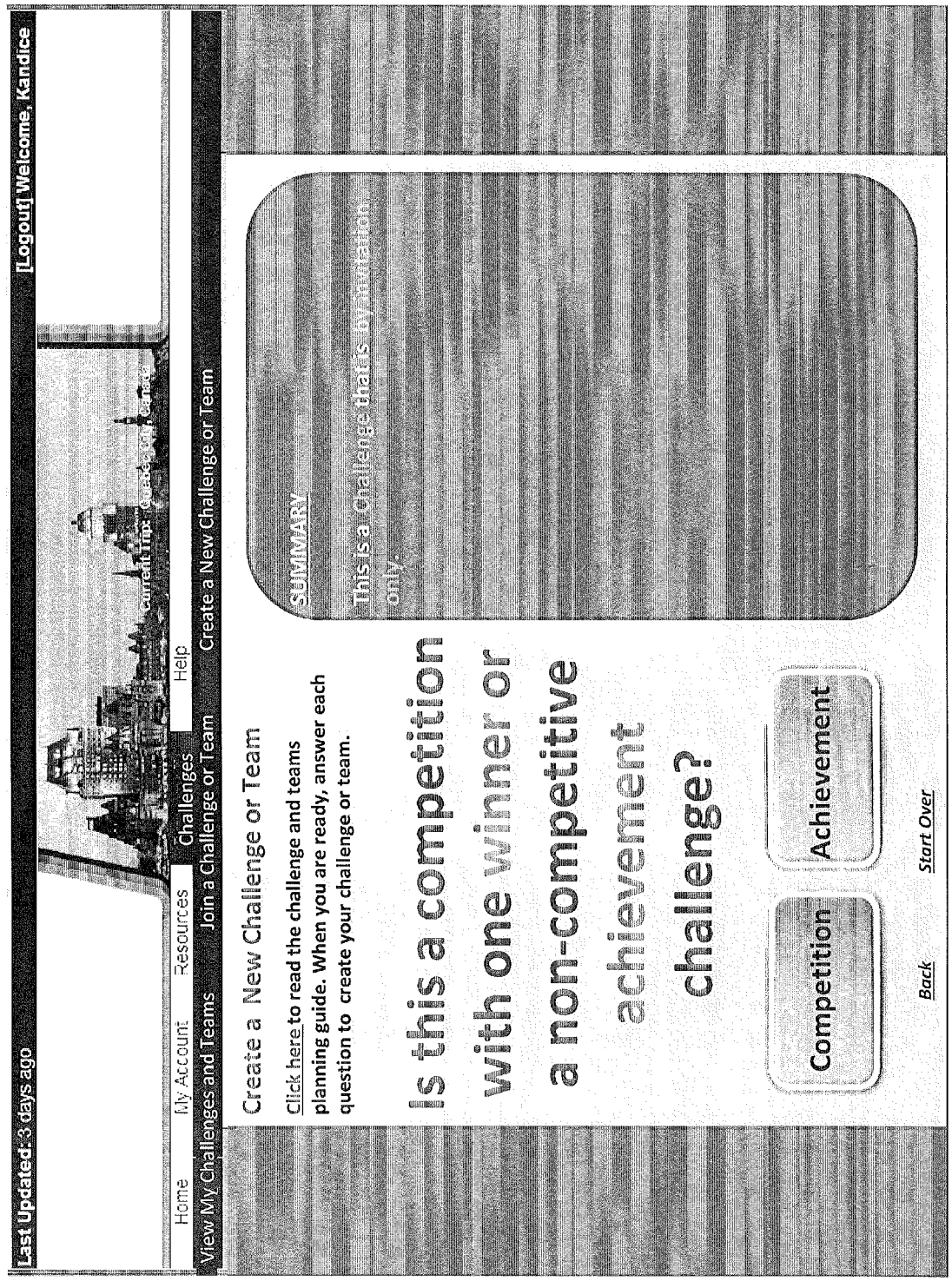
FIG. 34 is a screen shot illustrating exemplary aspects of the present invention.
Figure 35:
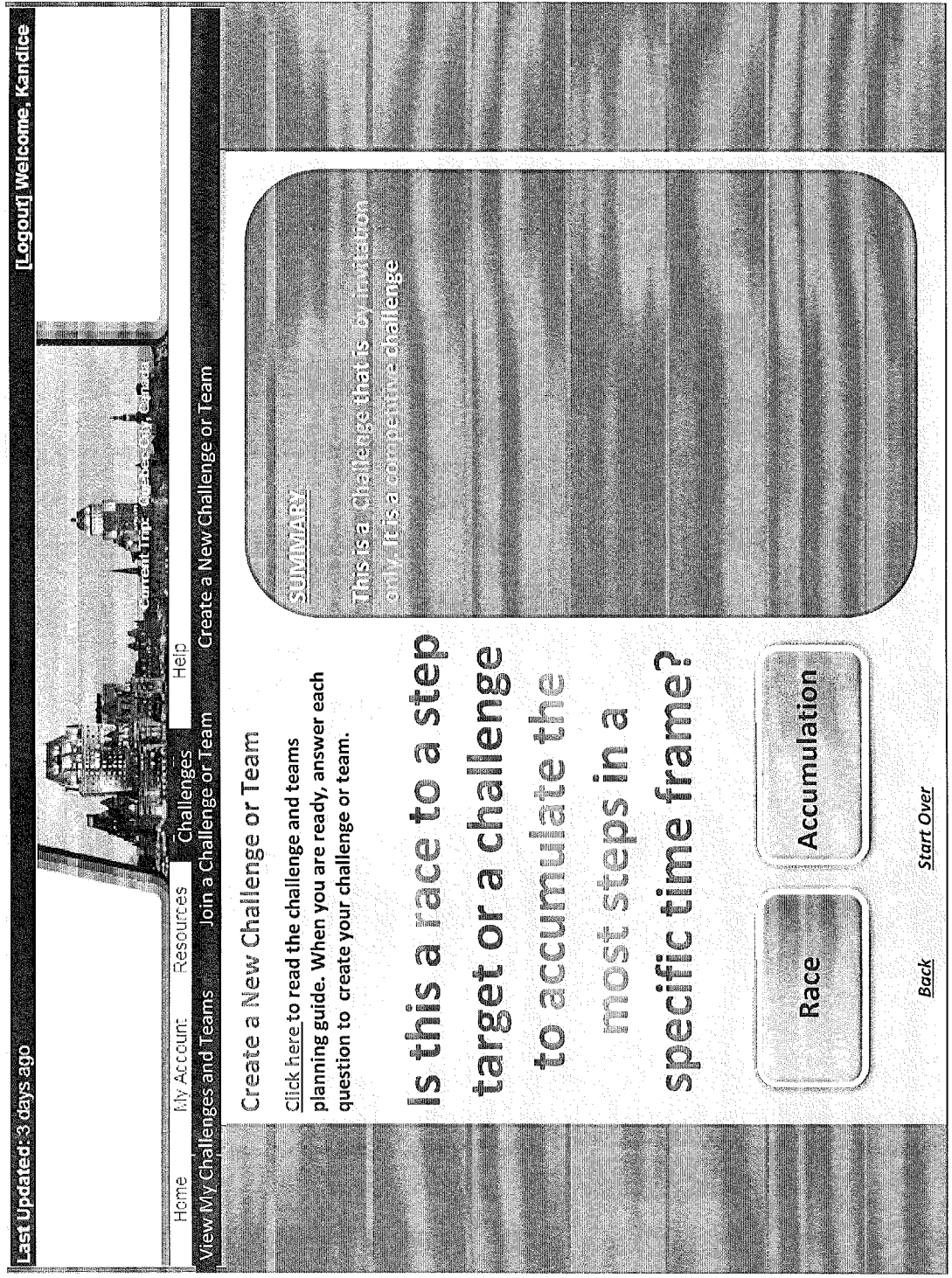
FIG. 35 is a screen shot illustrating exemplary aspects of the present invention.
Figure 36:
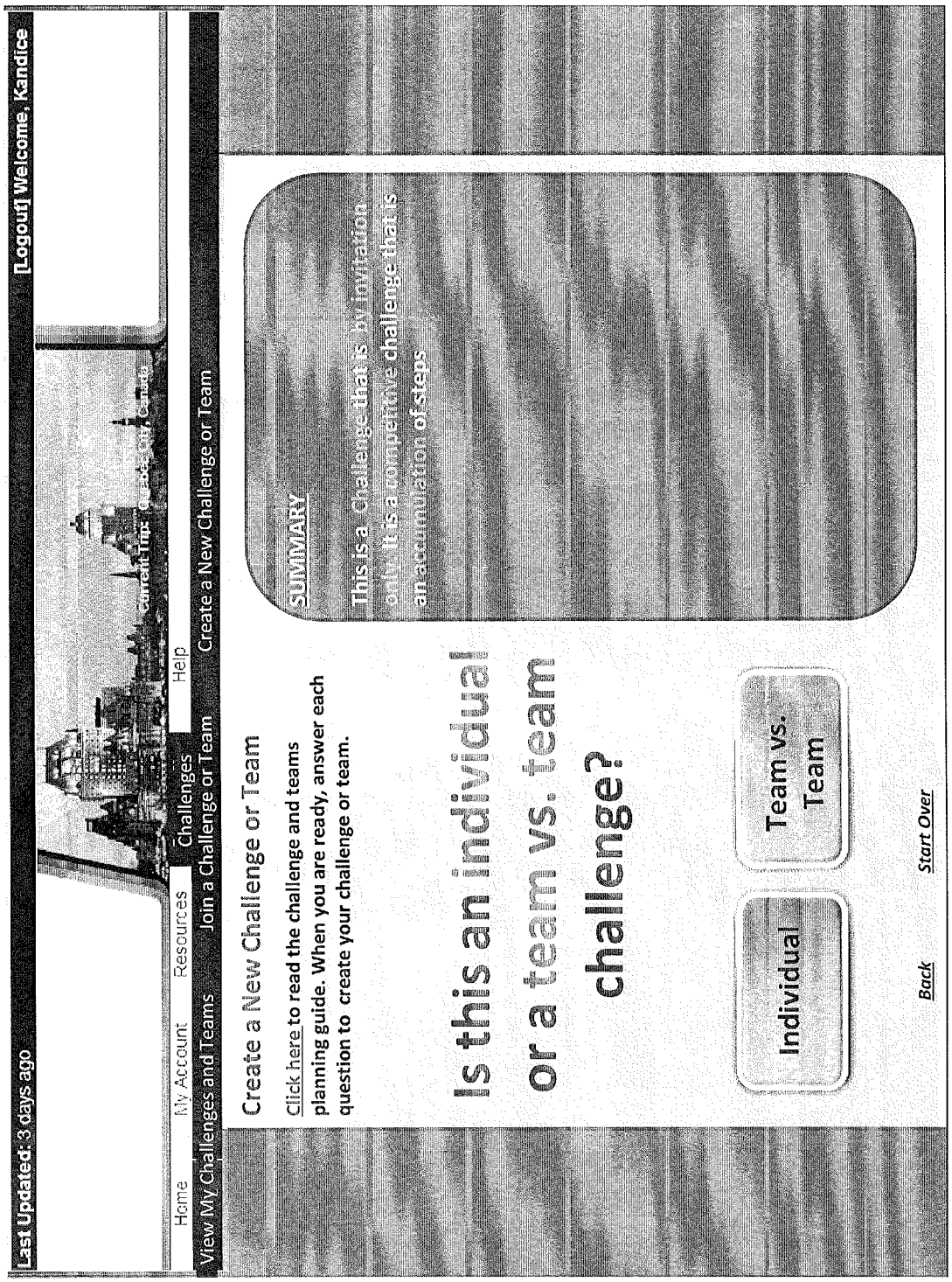
FIG. 36 is a screen shot illustrating exemplary aspects of the present invention.
Figure 40:
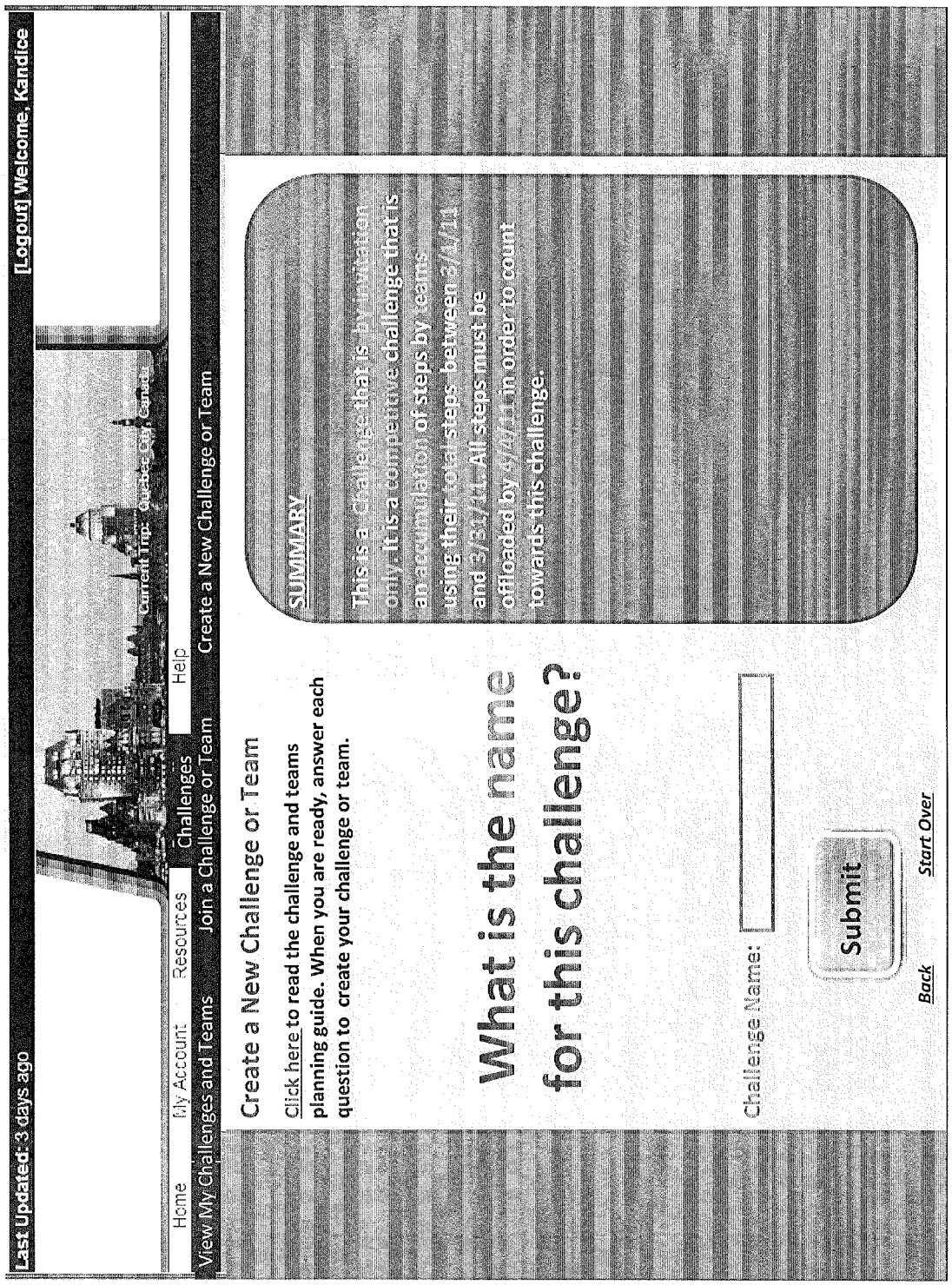
FIG. 40 is a screen shot illustrating exemplary aspects of the present invention.
Figure 42:
FIG. 42 is a screen shot illustrating exemplary aspects of the present invention.
Figure 43:
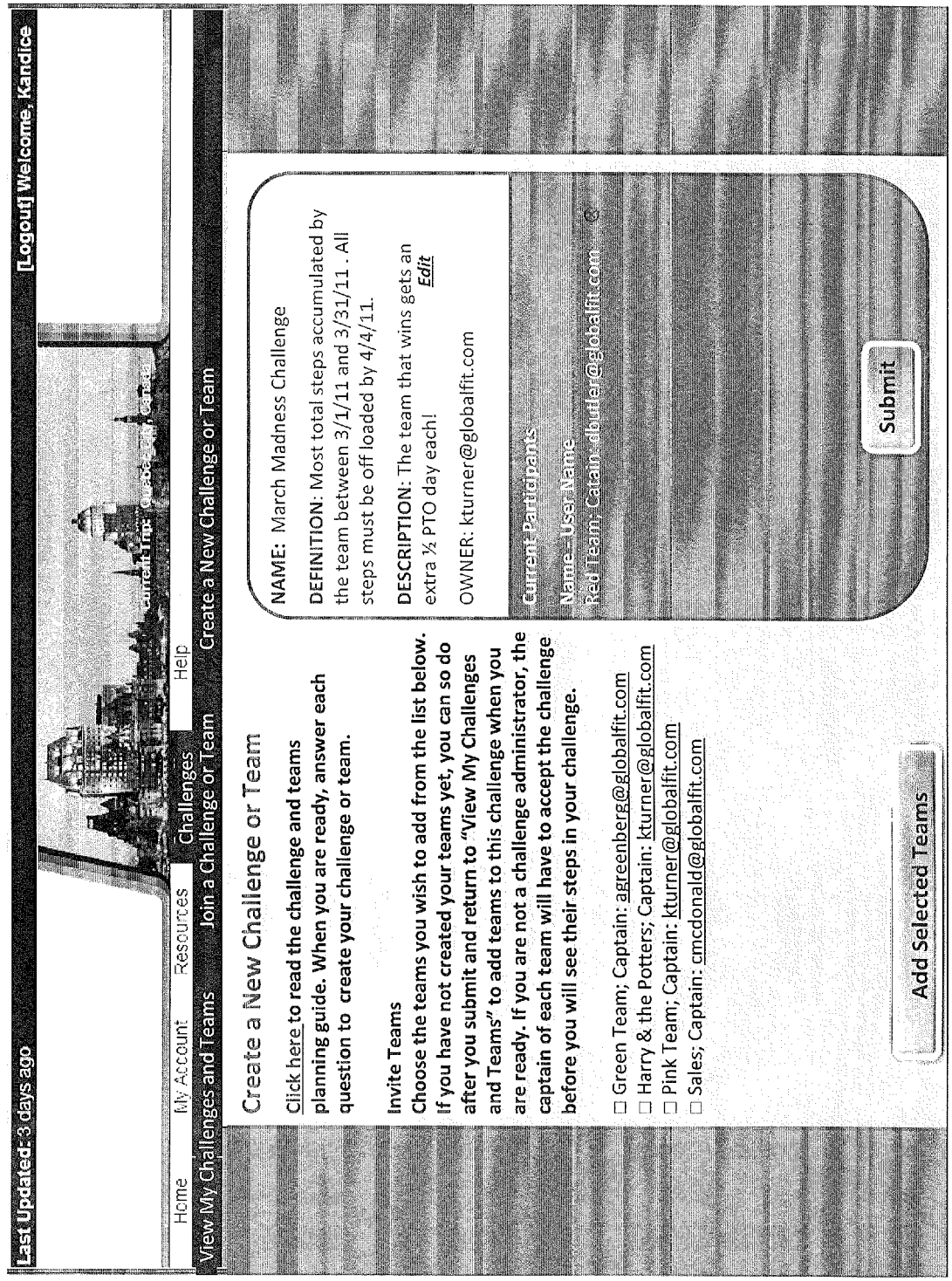
FIG. 43 is a screen shot illustrating exemplary aspects of the present invention.
Figure 44:
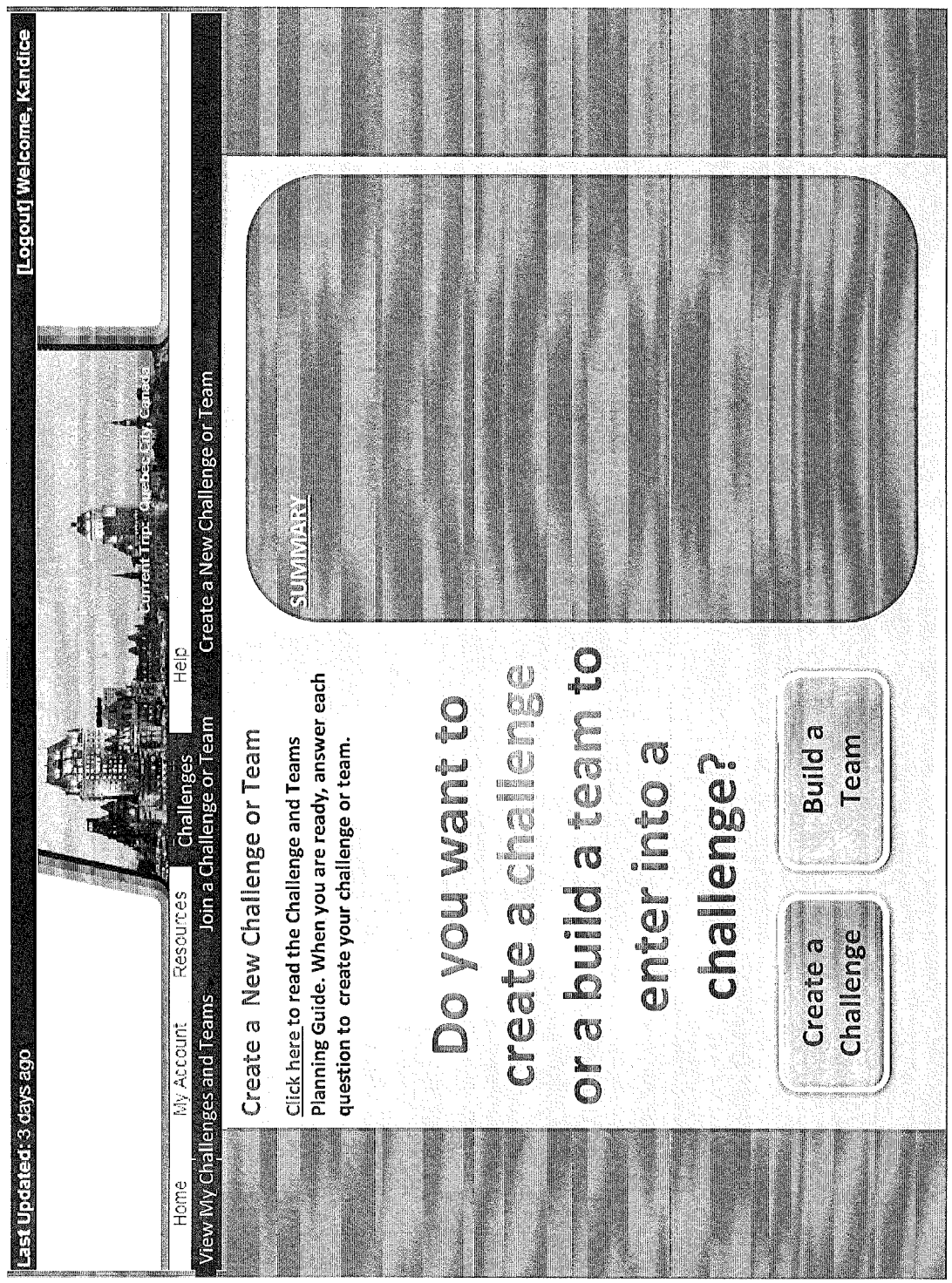
FIG. 44 is a screen shot illustrating exemplary aspects of the present invention.
Figure 45:
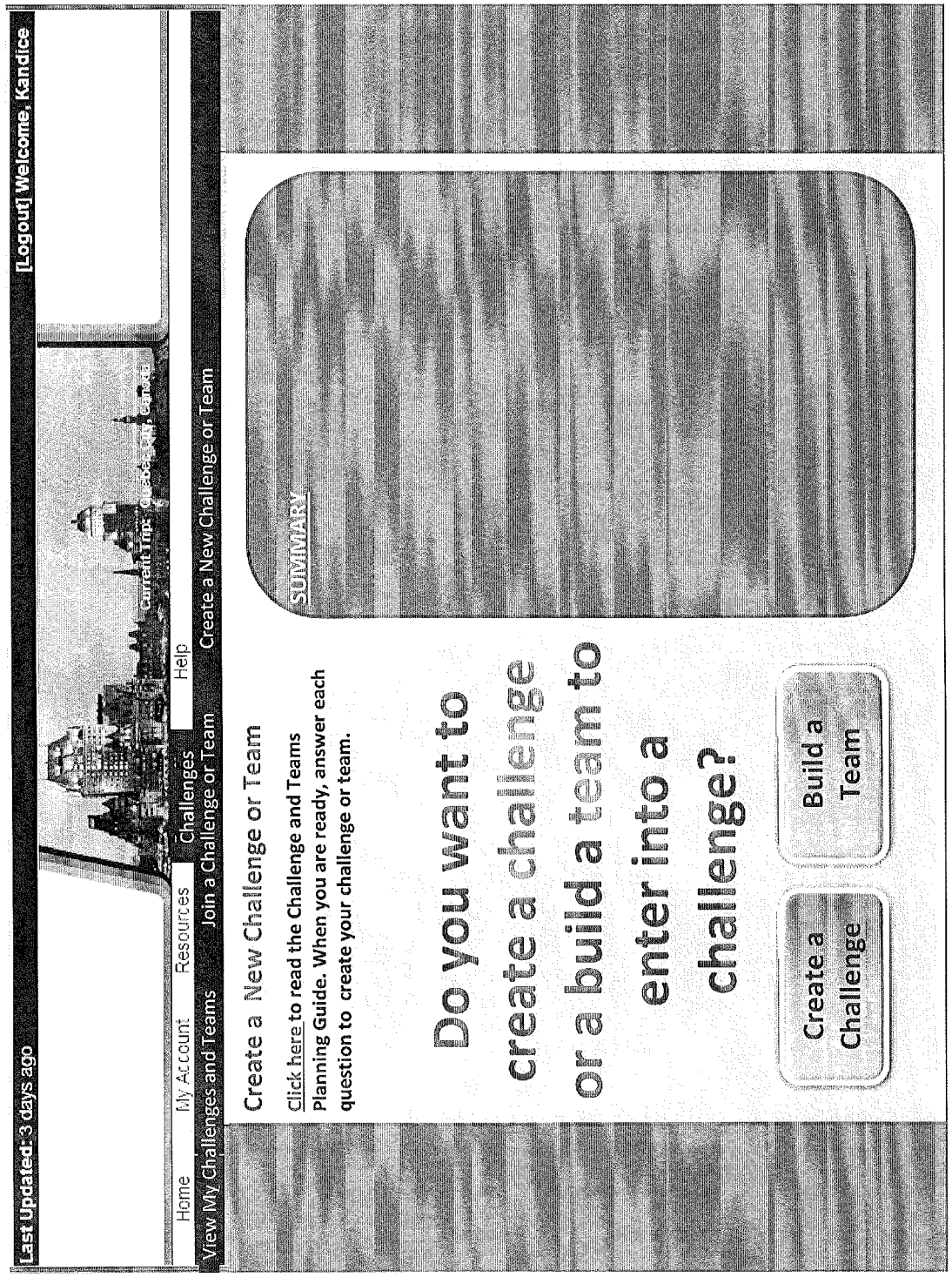
FIG. 45 is a screen shot illustrating exemplary aspects of the present invention.
Figure 46:
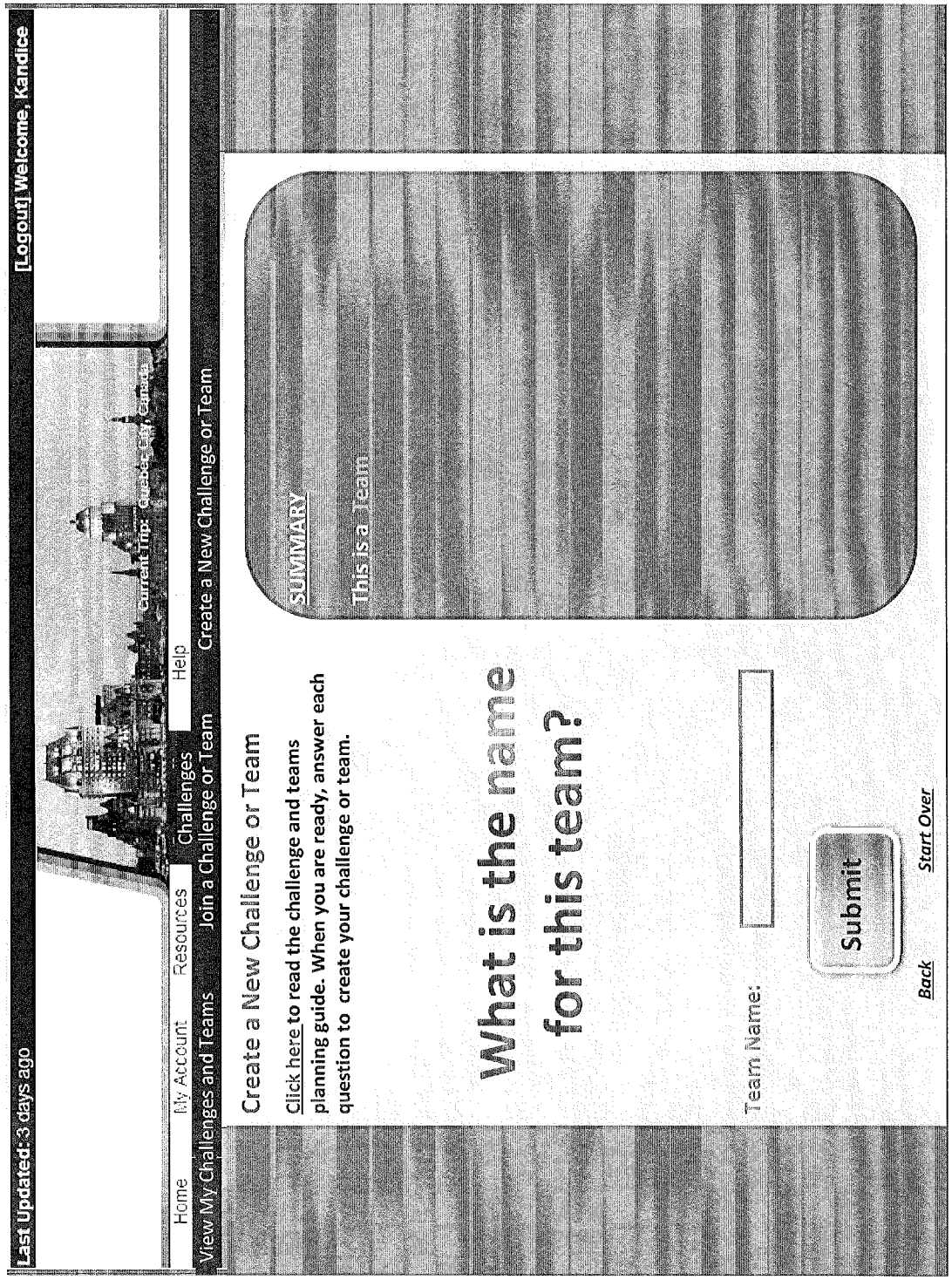
FIG. 46 is a screen shot illustrating exemplary aspects of the present invention.

As illustrated in FIG. 10, a graphical user interface (GUI) may be provided through computers 12 (including mobile device computers), for example, and may allow for access to the present invention by users, user-authorized reviewers, and administrators, for example. Although the GUI may be modified and/or "skinned" by a participating company, for example, the GUI may provide access to available challenges and teams. A user, for example, may access those challenges and/or teams in which the user participates, may join an available challenge or team, and may create a challenge or team and invite other users to participate.

Figure 11:
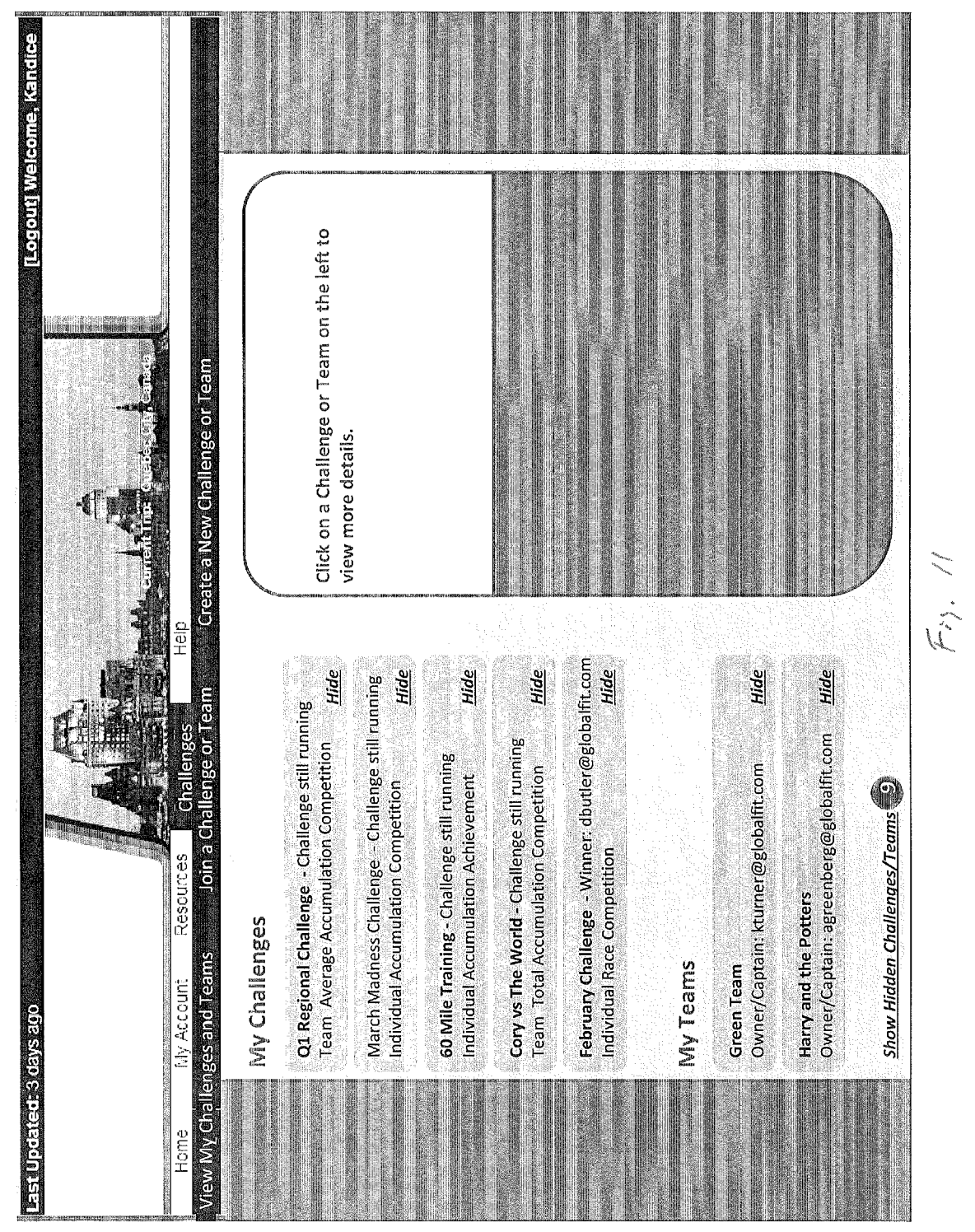

For example, as illustrated in FIG. 11, a user may view the challenges in which the user is participating and may access each challenge to view the details associated with the challenge. The challenges may be ordered alphabetically, by difficulty, by order of deadline for completion, by order of intended finish, by order of enrollment, or in like manner on the GUI and/or in the administrative recordation, such as at a database associated with a company server 16, for example. For example, if all challenges are still uncompleted, the challenge having the least amount of time left to complete the challenge, and/or the least amount of actions to be completed, may be listed first. Similarly, those challenges that have been completed but not yet deleted by the user may be listed first. Although a similar ordering may be applied to the listing of teams in which the user participates, the ordering of teams is preferably alphabetical.

Additional information may also be displayed, such as, for example, whether the challenge is still running or if the challenge is competitive (when a user is participating in the challenge with at least one other user) a winner or likely winner may be declared. Challenges completed and participated in by only one user may also be herein referred to as achievement challenges, and may provided different rewards and/or points accumulation than competitive challenges, for example. Challenges may take on any number of forms related to the accumulation of reward points, including, for example: the individual accumulation of reward points; the accumulation of reward points based on a team performance average; the accumulation of reward points based on total team performance in an individual race performance; the accumulation of reward points based on total team race performance; the accumulation of reward points based on individual average steps per day; the accumulation of reward points based on individual total steps, and team average and/or total steps.

Figure 12:
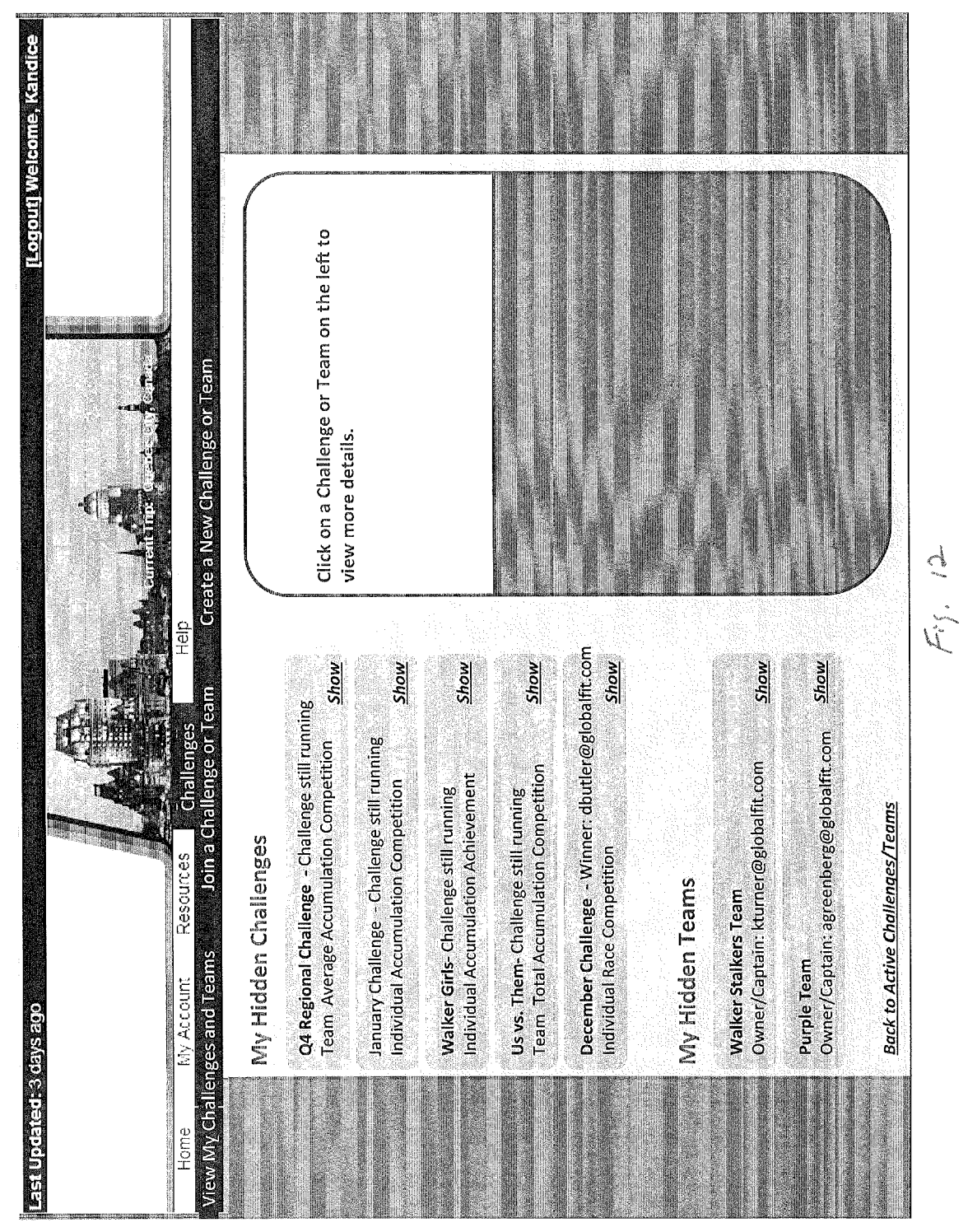

To organize the presentation of the challenges associated with the user, the GUI may further allow for the filtering and/or hiding of challenges. This may be done automatically, such as by elimination of completed challenges after a certain time has passed and/or by progress through a particular challenge. In any event, the information recorded for the user and/or team is not lost even if taken out of view. As illustrated in FIG. 12, the "hidden" challenges may be accessed via a separate page provided by the GUI and may be organized and/or filtered in the same manner as discussed above.

As illustrated in FIG. 13, an administrator and/or creator/owner of challenges may view individual challenges and the participants associated with each challenge. When an individual challenge is selected, information regarding the name of the challenge (as designated when creating the challenge), the attributes or definitions associated with the challenge (definitions with assigned variables may be designated when creating the challenge), the description of the challenge (as designated when creating the challenge), and the creator and/or owner of the challenge (such as the email address of the person who created the challenge, for example) may be entered, modified, requested, and/or listed.

The listing of participants in the selected challenge may include the participant's name, a company or other affiliation identifier, and an indication of progress within the challenge. For example, users many be listed in rank order from highest progression (or reward point accumulation) to lowest. In competitive challenges, a ranking number may be shown for each participant. For achievement challenges, no ranking number may be shown. For example, if the challenge is climbing stairs, each participant may have listed the number of steps climbed in a given period. If more participants are in a particular challenge, then a subset, such as the top 10, may be shown. In a user view, the "top 10" may be a selection of nine (9) other participants around the user to visually demonstrate to the user his or her place among the other participants.

An administrator/owner/creator may have the ability to delete users from the system and/or from a particular challenge. For example, the GUI may provide a red X, or delete symbol, for example, proximate to each participant that may allow an administrator/owner to remove participants from the challenge. Similarly, the data collected and/or associated with each of the users and/or the challenge itself may be exported outside the system, such as through Excel, for example.

This portion of the GUI may also allow for the inviting and/or assigning of potential participants to particular challenges. Similarly, the description and other attributes associated with the challenge or participants may be edited and or deleted. This functionality may also extend to individual participants and may allow for a participant to be deleted from the system entirely. A user of the system may optionally be provided with a similar view or views of the information described above, as illustrated in FIG. 14, but may be restricted from any editing functions.

Figure 15:
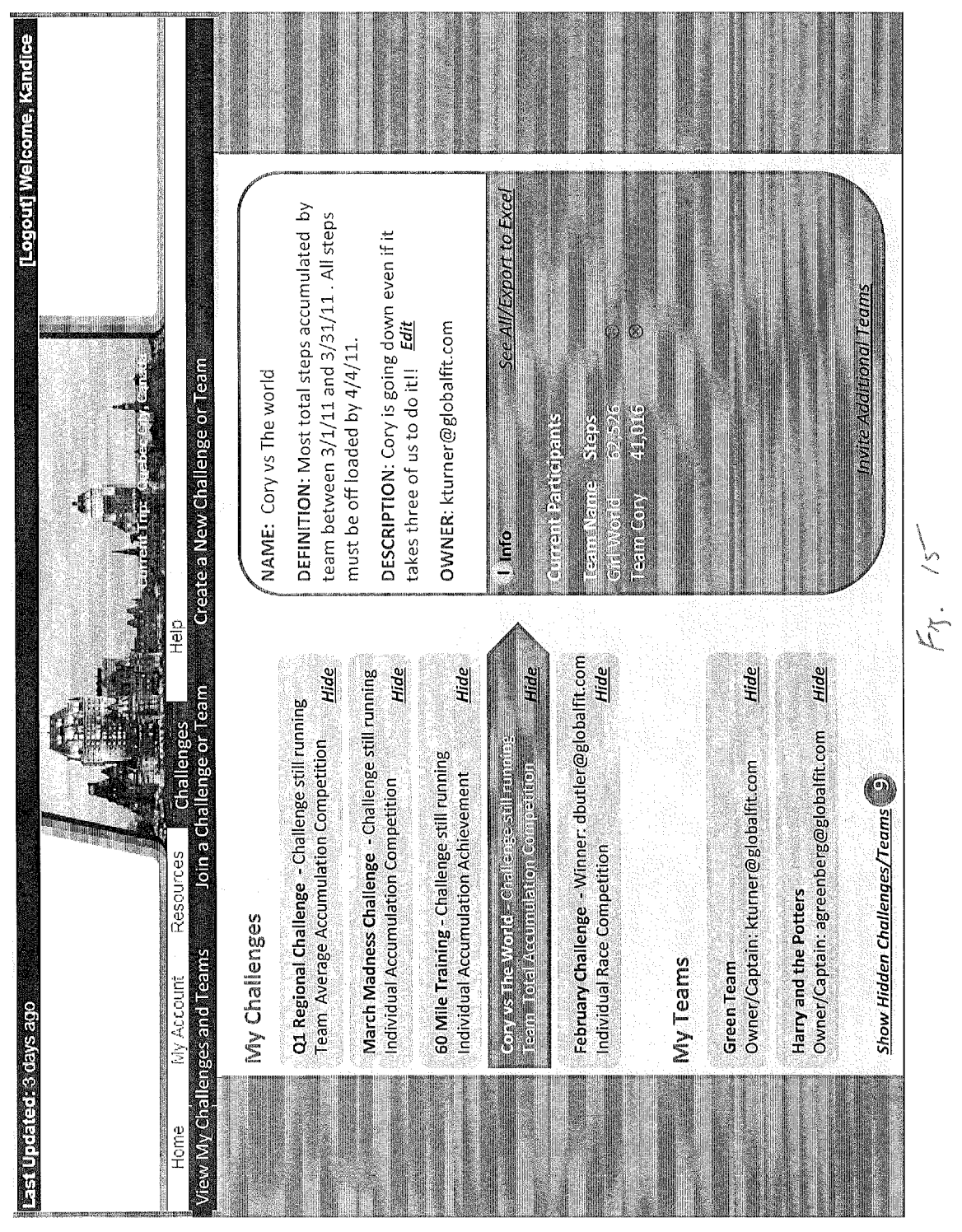
Figure 16:
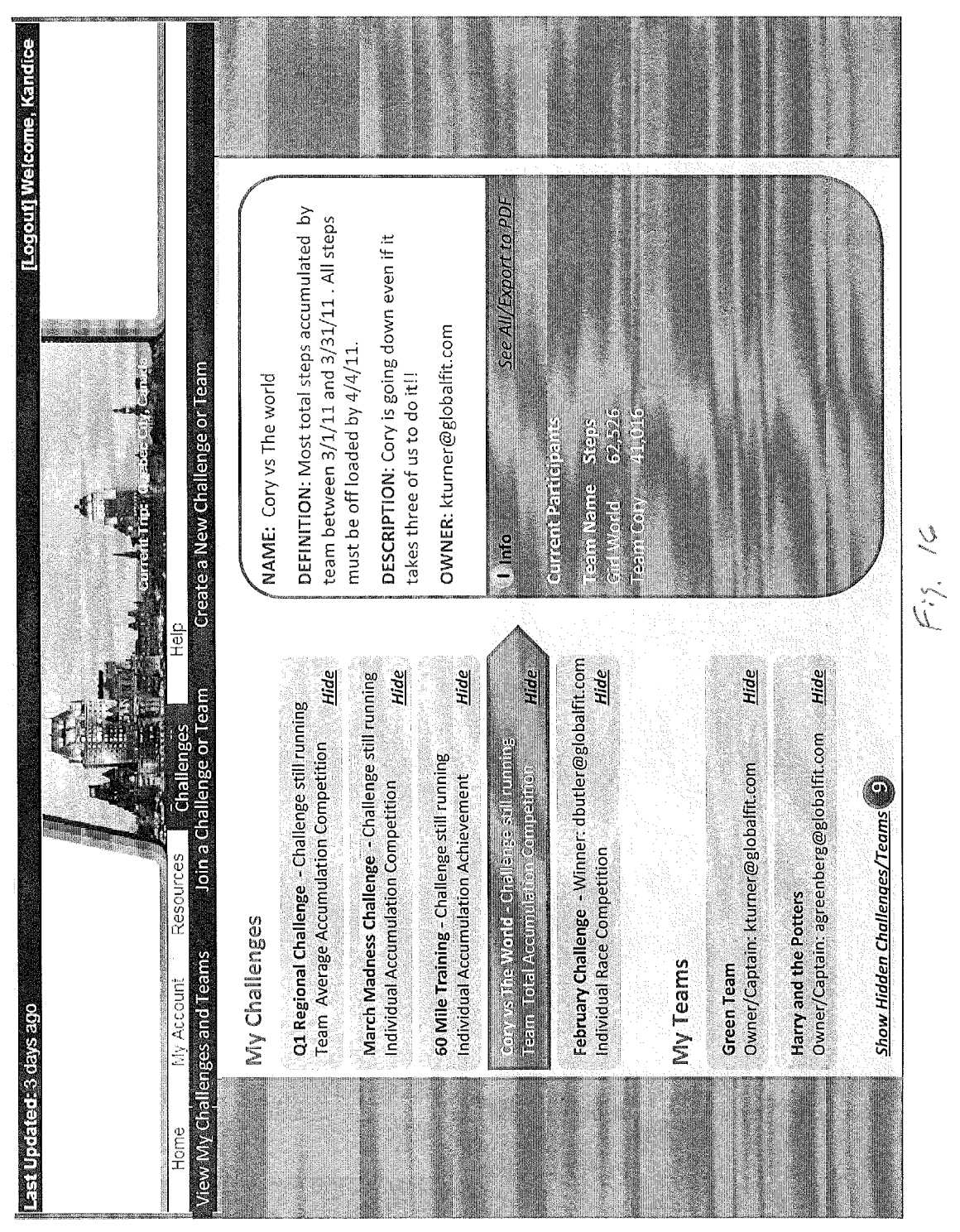
Figure 17:
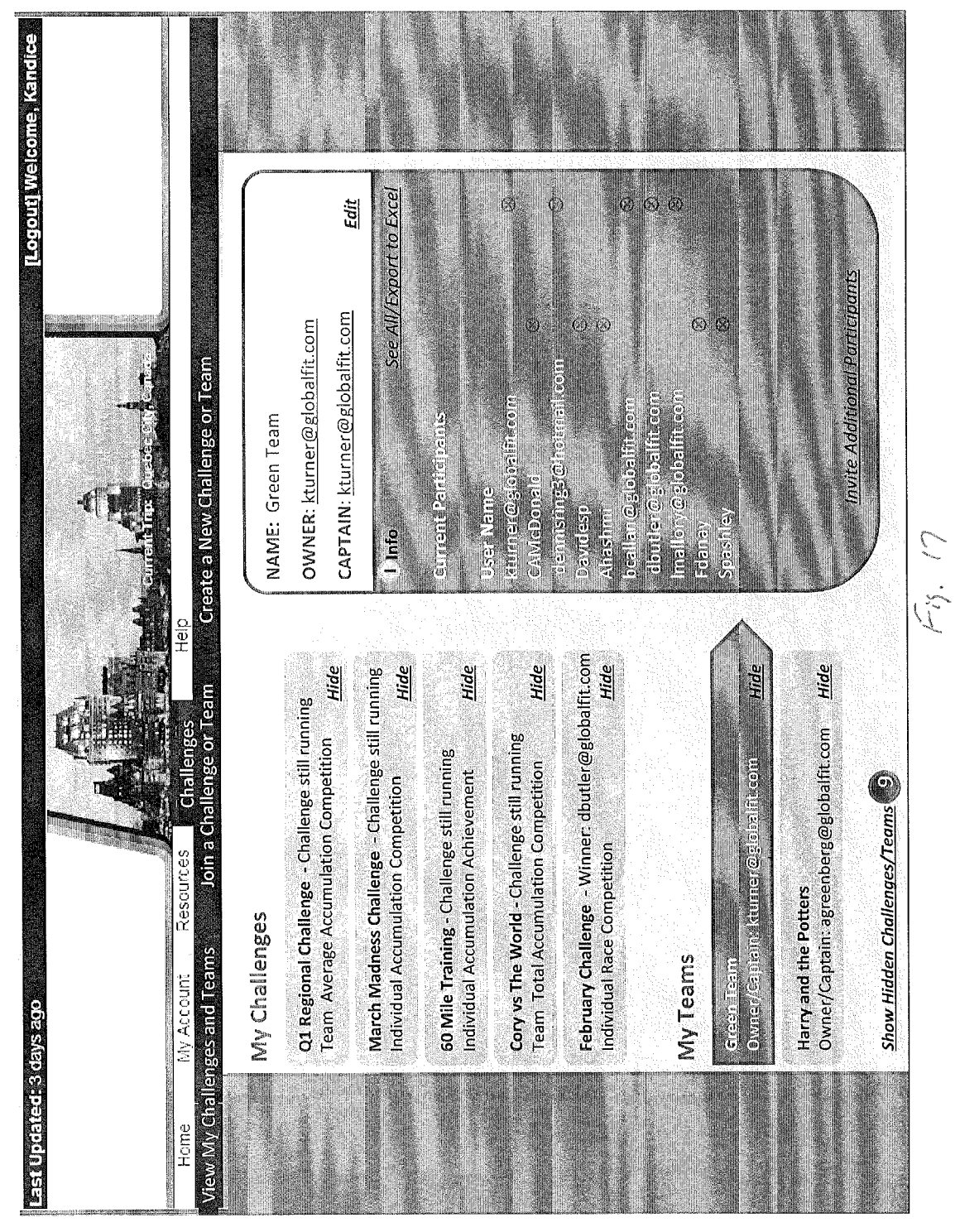

As with individual challenge information, team information may be similarly displayed, as illustrated in FIGS. 15 and 16. As illustrated in FIG. 17, team information may be displayed to allow for ease of control by the team captain and/or an administrator or owner/creator. For example, the GUI may provide information including the name if each participant, the name of the team (as designated when creating the challenge), the owner/creator (the person who created the team), and the captain (as designated when creating the team), for example. The participants may be listed alphabetically, for example, and may be associated with a user name and/or contact information, such as an email address, for example. In addition to the editing controls discussed above, the information and particulars of each participant, whether or not displayed within the GUI, may be exported by an authorized user. Similarly, additional participants may be invited to a team whether preexisting in the system or not.

Figure 18:
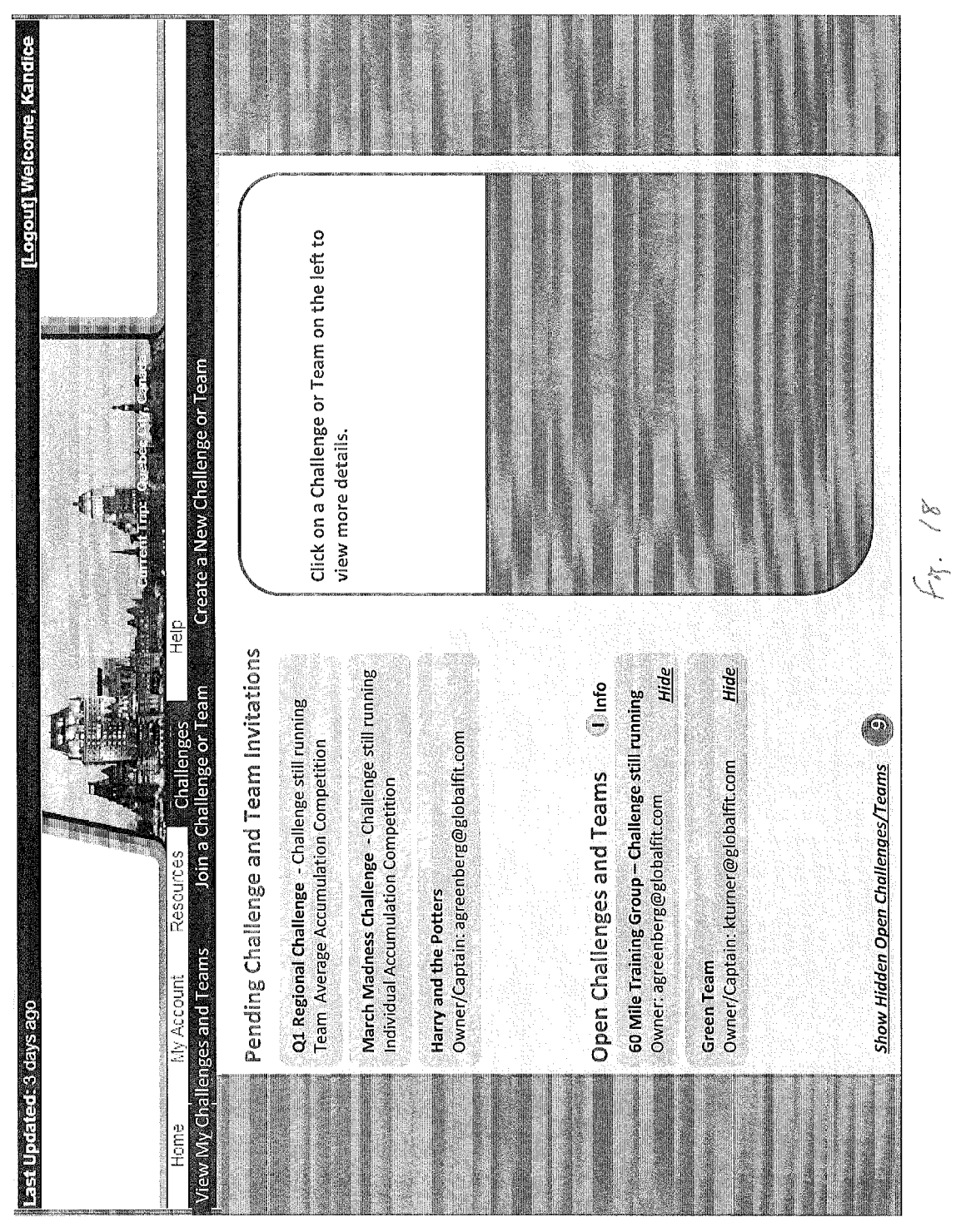
Figure 19:
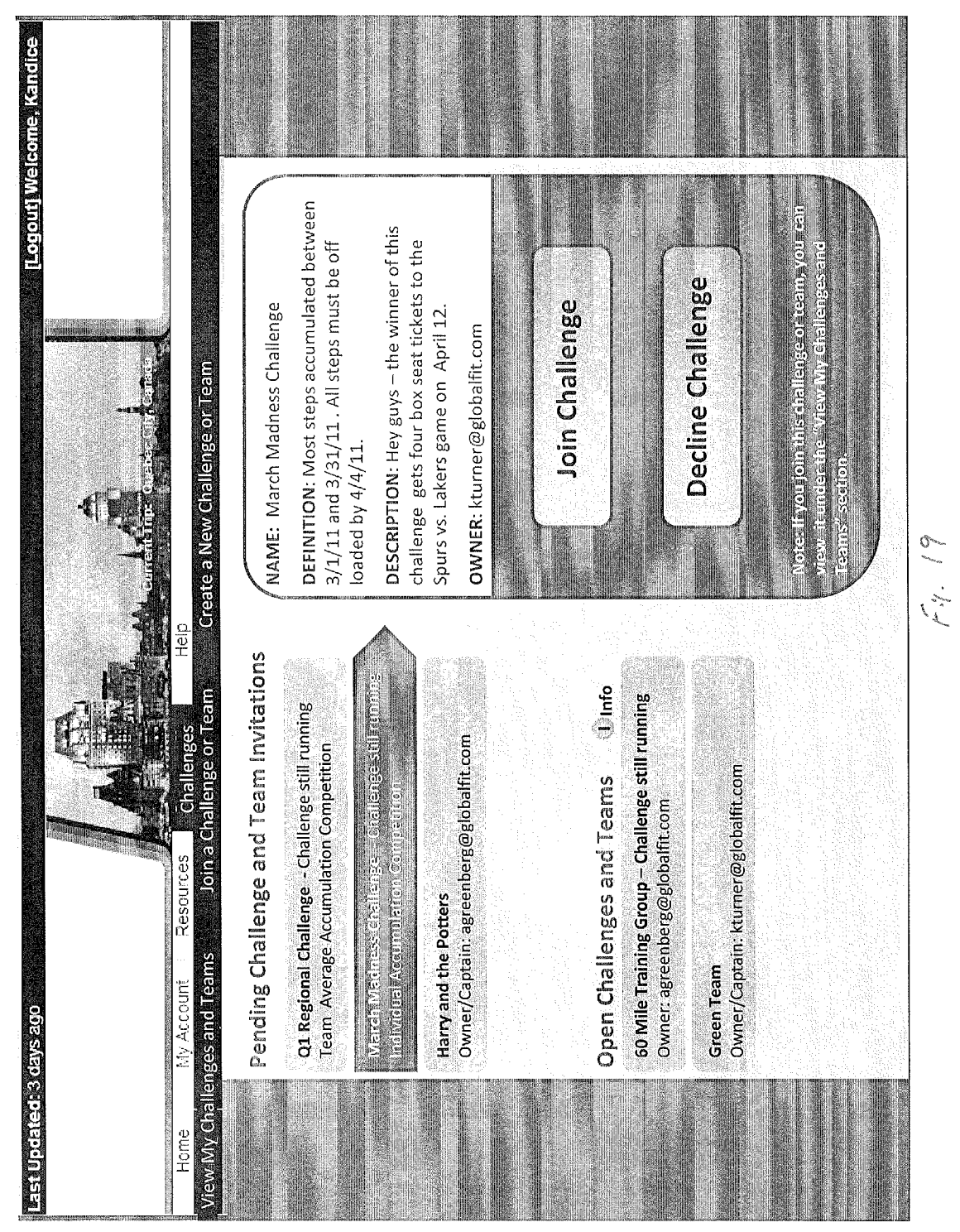

A user seeking to join a challenge and/or team (otherwise not created by the user), may begin through a challenge access page as illustrated in FIG. 18. For example, the GUI may provide a "Join a Challenge or Team" link which may be clicked by a user, and which may, upon being clicked, further present to the user pending and/or available challenges and teams within the system. As further illustrated in FIG. 19, the user may click to join a presented challenge and/or team, and/or to access more information about each. After a user initiates a request to participate in a team, for example, the captain of the requested team may accept or deny the participant. Similarly, other users and/or teams may request that a particular team participate in a particular challenge, which may be accepted or denied by the team captain.

Figure 50:
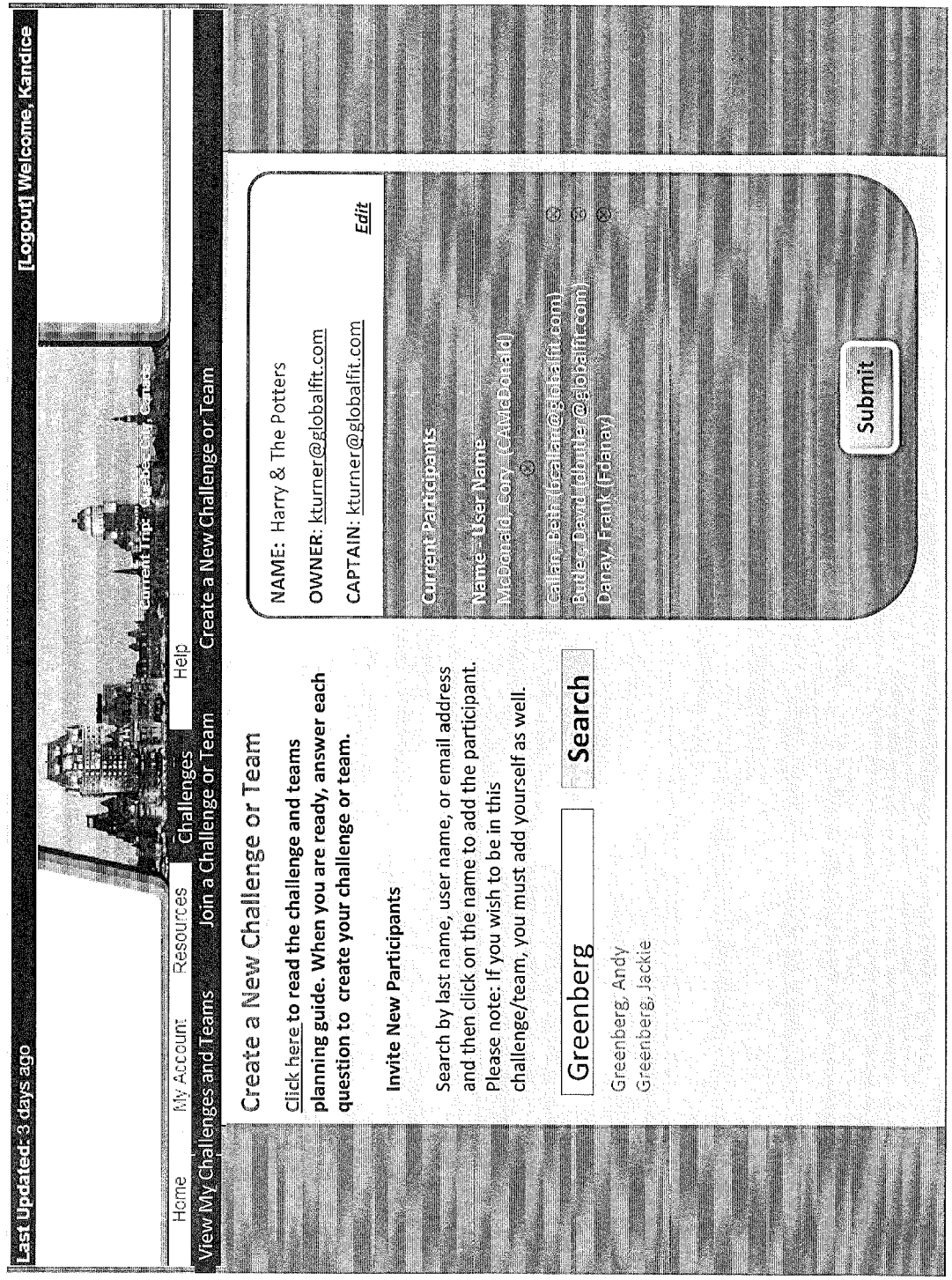
FIG. 50 is a screen shot illustrating exemplary aspects of the present invention.

As illustrated in FIGS. 20-50, challenges and/or teams may be added by a user of the system by entering information through, for example, prompting by portions of the GUI. The creator of a challenge may set start and end dates, for example, and set deadlines for which participants must have their progress reported into the system. As illustrated in FIG. 30, participants may be selected for a challenge as individuals or for a team, and may be selected from a list of possible participants. Similarly, as illustrated in FIG. 50, for example, a search may be done for potential participants within the system and/or from third party participating locations. Although not shown, the present invention may, as would be appreciated by those skilled in the art, access social networks over network environment 14 for both inviting participants and/or posting or updating of challenge results.

For example, a company that employs the present invention may list those individuals wishing to participate in one or more challenges in the present invention. Individual participants may further limit the challenges in which their respective name may be selected and/or presented. For example, an individual with poor knees may wish not to be invited to challenges involving stairs or running. Likewise, a participant with an affinity for bike riding may wish to limit participation to those challenges involving bike riding.

Similarly, challenges may be increased in difficultly and/or duration depending on the participants(s) and/or the rate of progress, for example, through the challenge. Such changes to challenges, and original challenges for that matter, may be appropriately posted to a participants' GUI interface page, social network and/or electronic calendar. For example, when a participant signs-up for a challenge which requires a certain amount of daily performance, for example, the present invention may post a daily reminder to the participant's electronic calendar reminding the participant of the challenge. The calendar posting may also take into account the participant's known preferences and/or other events within the participant's calendar and may propose a time for the participant to exercise.

It will be understood that the embodiment of the present invention that is illustrated and described is merely exemplary and that a person skilled in the art can make many variations to that embodiments. All such embodiments are intended to be included within the scope of the present invention as defined by the claims.

What is claimed is:

1. A system for tracking physical activity, comprising:
    a non-transitory computer readable storage medium having encoded thereon computer executable instructions for receiving, via at least one network connection, participant information, wherein the participant information comprises at least one identification code of the participant, a participant location, a participant title, and a participant affiliation;
    a rules engine communicatively connected to said computer executable instructions, and comprising a plurality of rules to generate at least one challenge for a plurality of the participants uniquely in accordance with the participant information of each of the participants; and
    at least one tracking means associated with each of the participants and coupled to the rules engine for correlating tracked progress of each of the participants, by the participant information, with the at least one challenge.

2. The system of claim 1, wherein the at least one challenge is a physical activity.

3. The system of claim 1, wherein the at least one challenge is between at least two participants.

4. The system of claim 3, wherein at least one participant is declared a winner of the at least one challenge.

5. The system of claim 1, wherein the at least one challenge is virtual.

6. The system of claim 1, wherein at least one reward is provided to a participant upon completion of at least one challenge.

7. The system of claim 1, wherein at least one reward is provided to a participant based upon the performance of the participant.

8. The system of claim 1, wherein the at least one challenge is virtual.

9. The system of claim 1, wherein at least one reward is provided to a participant upon completion of at least one challenge in accordance with the information.

10. The system of claim 1, wherein at least one reward is provided to a participant based upon the performance of the participant.

11. The system of claim 1, wherein the information maybe provided to at least one social network associated with the participant.

12. A system for tracking physical activity, comprising:
a non-transitory computer readable storage medium having encoded thereon computer executable instructions for receiving, via at least one network connection, participant information, wherein the participant information comprises at least one identification code of the participant, a participant location, a participant title, and a participant affiliation;
a rules engine communicatively connected to said computer executable instructions, and comprising a plurality of rules to generate at least one challenge for a plurality of the participants uniquely in accordance with the participant information of each of the participants;
at least one portable monitoring unit associated with the at least one identification code;
at least one remote transceiver communicatively optionally coupled to at least one portable monitoring unit and the network connection; and
wherein information from the at least one portable monitoring unit is correlated with at least one challenge and is indicative of a performance of the participant in the at least one challenge.

13. The system of claim 12, wherein the at least one challenge is a physical activity.

14. The system of claim 12, wherein the at least one challenge is between at least two participants.

15. The system of claim 14, wherein at least one participant is declared a winner of the at least one challenge.

* * * * *